US010278563B2

(12) United States Patent
Ouyang et al.

(10) Patent No.: US 10,278,563 B2
(45) Date of Patent: May 7, 2019

(54) HANDHELD SURGICAL ENDOSCOPE WITH DETACHABLE CANNULA

(71) Applicants: Xiaolong Ouyang, Bellevue, WA (US); Robert K. Deckman, San Bruno, CA (US); Chih-Yu Ting, New Taipei (TW); Shih-Ping Wang, Palo Alto, CA (US)

(72) Inventors: Xiaolong Ouyang, Bellevue, WA (US); Robert K. Deckman, San Bruno, CA (US); Chih-Yu Ting, New Taipei (TW); Shih-Ping Wang, Palo Alto, CA (US)

(73) Assignee: UROVIU CORP., Bellevue, WA (US)

( * ) Notice: Subject to any disclaimer, the term of this patent is extended or adjusted under 35 U.S.C. 154(b) by 0 days.

(21) Appl. No.: 15/651,526

(22) Filed: Jul. 17, 2017

(65) Prior Publication Data
US 2018/0256009 A1 Sep. 13, 2018

Related U.S. Application Data

(63) Continuation-in-part of application No. 15/462,331, filed on Mar. 17, 2017, and a continuation-in-part of
(Continued)

(51) Int. Cl.
A61B 1/00 (2006.01)
A61B 1/05 (2006.01)
A61B 1/06 (2006.01)

(52) U.S. Cl.
CPC ...... A61B 1/00048 (2013.01); A61B 1/00016 (2013.01); A61B 1/00034 (2013.01);
(Continued)

(58) Field of Classification Search
CPC ............ A61B 1/00048; A61B 1/00016; A61B 1/00034; A61B 1/00052; A61B 1/00103; A61B 1/05; A61B 1/0684
(Continued)

(56) References Cited

U.S. PATENT DOCUMENTS 5,188,093 A 2/1993 Lafferty
5,323,767 A * 6/1994 Lafferty ............. A61B 1/00096
600/109
(Continued)

FOREIGN PATENT DOCUMENTS

WO WO2012/060932 5/2012
WO WO2012060932 5/2012
(Continued)

OTHER PUBLICATIONS

Jul. 12, 2016 International Search Report and Written Opinion in connection with corresponding International Application No. PCT/US2016/18670.

Primary Examiner — John P Leubecker
Assistant Examiner — William B Chou
(74) Attorney, Agent, or Firm — Cooper & Dunham LLP

(57) ABSTRACT

A handheld surgical endoscope has a disposable, single-use portion that includes a fluid hub and cannula, and a re-usable portion that includes a handle and display module. The distal tip includes LED illumination and an imaging module that feeds live video to the display module. The single-use and re-usable portions mate and un-mate with each other via physically separated mechanical and electrical connectors. The surgical endoscope is configured for operation by a single clinician in many procedures.

15 Claims, 20 Drawing Sheets

Related U.S. Application Data application No. 15/371,858, filed on Dec. 7, 2016, now Pat. No. 9,895,048, and a continuation-in-part of application No. PCT/US2016/018670, filed on Feb. 19, 2016, which is a continuation-in-part of application No. 14/913,867, filed as application No. PCT/US2016/018670 on Feb. 19, 2016, said application No. 15/462,331 is a continuation-in-part of application No. 14/913,867, filed on Feb. 23, 2016, and a continuation-in-part of application No. PCT/US2016/065396, filed on Dec. 7, 2016, which is a continuation-in-part of application No. 14/913,867, filed on Feb. 23, 2016, and a continuation-in-part of application No. PCT/US2016/018670, filed on Feb. 19, 2016, said application No. 15/462,331 is a continuation-in-part of application No. PCT/US2016/018670, filed on Feb. 19, 2016, said application No. PCT/US2016/065396 is a continuation-in-part of application No. 15/371,858, filed on Dec. 7, 2016, now Pat. No. 9,895,048.

(60) Provisional application No. 62/339,810, filed on May 21, 2016, provisional application No. 62/362,643, filed on Jul. 15, 2016, provisional application No. 62/375,814, filed on Aug. 16, 2016, provisional application No. 62/405,930, filed on Oct. 9, 2016, provisional application No. 62/416,403, filed on Nov. 2, 2016, provisional application No. 62/443,769, filed on Jan. 8, 2017, provisional application No. 62/449,257, filed on Jan. 23, 2017, provisional application No. 62/452,883, filed on Jan. 31, 2017, provisional application No. 62/275,222, filed on Jan. 5, 2016, provisional application No. 62/275,241, filed on Jan. 6, 2016, provisional application No. 62/279,784, filed on Jan. 17, 2016, provisional application No. 62/287,901, filed on Jan. 28, 2016, provisional application No. 62/299,453, filed on Feb. 24, 2016, provisional application No. 62/119,521, filed on Feb. 23, 2015, provisional application No. 62/120,316, filed on Feb. 24, 2015, provisional application No. 62/139,754, filed on Mar. 29, 2015, provisional application No. 62/254,718, filed on Nov. 13, 2015, provisional application No. 62/259,991, filed on Nov. 25, 2015.

(52) U.S. Cl.
CPC ...... *A61B 1/00052* (2013.01); *A61B 1/00103* (2013.01); *A61B 1/05* (2013.01); *A61B 1/0684* (2013.01)

(58) Field of Classification Search
USPC ....... 600/104, 109, 112, 114, 120, 129, 130, 600/131, 133, 136, 138, 139, 152, 153, 600/156, 160, 178, 179, 182
See application file for complete search history.

(56) References Cited

U.S. PATENT DOCUMENTS

| | | | |
|---|---|---|---|
| 5,329,936 A * | 7/1994 | Lafferty | A61B 1/00096 600/109 |
| 5,486,155 A | 1/1996 | Muller | |
| 5,860,953 A | 1/1999 | Snoke | |
| 5,928,137 A | 7/1999 | Green | |
| 5,935,141 A | 10/1999 | Weldon | |
| 6,174,307 B1 * | 1/2001 | Daniel | A61B 1/00098 600/103 |
| 6,221,007 B1 * | 4/2001 | Green | A61B 1/00052 600/104 |
| 7,798,995 B2 | 9/2010 | Yue | |
| 8,187,171 B2 | 5/2012 | Irion | |
| 8,460,182 B2 | 6/2013 | Ouyang et al. | |
| 8,696,552 B2 | 4/2014 | Whitman | |
| 8,803,960 B2 | 8/2014 | Sonnenschein | |
| 2001/0007051 A1 | 7/2001 | Nakashima | |
| 2004/0162572 A1 * | 8/2004 | Sauer | A61B 10/04 606/170 |
| 2005/0085695 A1 | 4/2005 | Shener et al. | |
| 2005/0154262 A1 | 7/2005 | Banik | |
| 2005/0177027 A1 | 8/2005 | Hirata | |
| 2006/0114986 A1 | 6/2006 | Knapp | |
| 2006/0173245 A1 | 8/2006 | Todd et al. | |
| 2007/0162095 A1 | 7/2007 | Kimmel | |
| 2008/0071144 A1 | 3/2008 | Fein | |
| 2008/0108869 A1 | 5/2008 | Sanders | |
| 2008/0225410 A1 | 9/2008 | Ning | |
| 2011/0009694 A1 | 1/2011 | Schultz et al. | |
| 2011/0063428 A1 | 3/2011 | Sonnenschein | |
| 2012/0040305 A1 | 2/2012 | Karazivan | |
| 2012/0100729 A1 | 4/2012 | Edidin | |
| 2012/0289858 A1 | 11/2012 | Ouyang et al. | |
| 2013/0150672 A1 | 6/2013 | Fujitani | |
| 2013/0035553 A1 | 7/2013 | Konstorum | |
| 2013/0345514 A1 | 12/2013 | Manion | |
| 2014/0022649 A1 | 1/2014 | Eckhardt | |
| 2014/0107416 A1 | 4/2014 | Birnkrant | |
| 2014/0180007 A1 | 6/2014 | Edidin | |
| 2014/0228635 A1 | 8/2014 | Tuliakov | |
| 2015/0005575 A1 | 1/2015 | Kobayashi | |
| 2015/0018622 A1 | 1/2015 | Tesar et al. | |
| 2015/0150441 A1 | 6/2015 | Ouyang | |
| 2015/0196197 A1 * | 7/2015 | Kienzle | A61B 1/042 600/478 |
| 2016/0073853 A1 | 3/2016 | Venkatesan | |
| 2016/0334694 A1 | 11/2016 | Liu | |
| 2017/0086651 A1 | 3/2017 | Sato | |
| 2017/0295347 A1 | 10/2017 | Schneider | |
| 2017/0310858 A1 | 10/2017 | Mueckl | |

FOREIGN PATENT DOCUMENTS

| | | |
|---|---|---|
| WO | WO2014/031192 | 2/2014 |
| WO | WO2014031192 | 2/2014 |
| WO | WO2014/065901 | 5/2014 |
| WO | WO2014/065901 | 5/2015 |

* cited by examiner

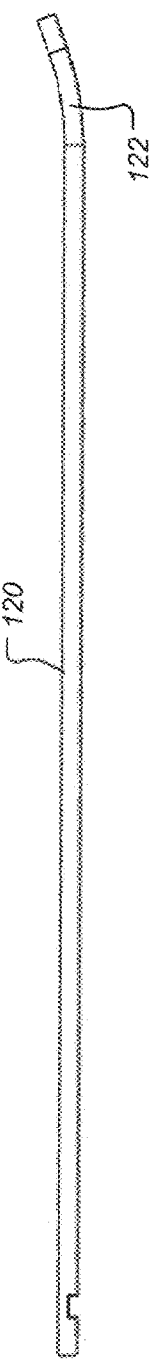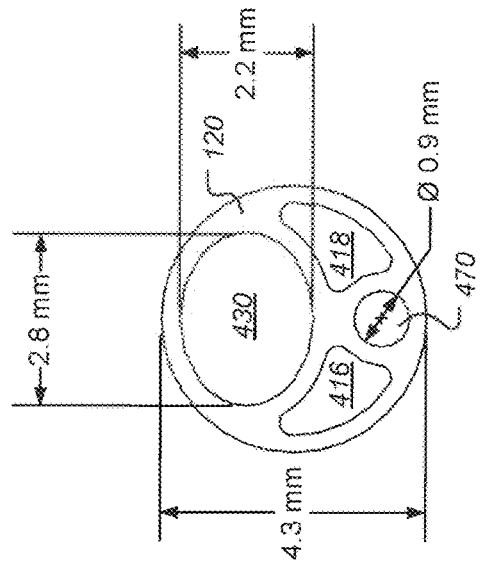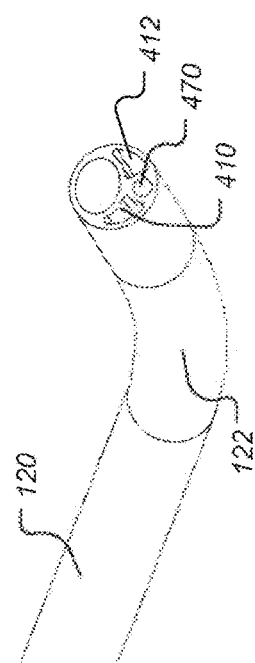
FIG. 4A
FIG. 4C
FIG. 4B

HANDHELD SURGICAL ENDOSCOPE WITH DETACHABLE CANNULA

REFERENCE TO RELATED APPLICATIONS

This patent application claims the benefit of and incorporates by reference each of the following provisional applications:
U.S. Prov. Ser. No. 62/513,386 filed May 31, 2017;
U.S. Ser. No. 62/530,238 filed Jul. 9, 2017; and
U.S. Prov. Ser. No. 62/531,212 filed Jul. 11, 2017.
This patent application is a continuation-in-part of and incorporates by reference the following patent application:
U.S. Ser. No. 15/462,331 filed Mar. 17, 2017, which claims the benefit of and incorporates by reference each of the following provisional applications:
U.S. Prov. Ser. No. 62/339,810 filed May 21, 2016;
U.S. Prov. Ser. No. 62/362,643 filed Jul. 15, 2016;
U.S. Prov. Ser. No. 62/375,814 filed Aug. 16, 2016;
U.S. Prov. Ser. No. 62/405,930 filed Oct. 9, 2016;
U.S. Prov. Ser. No. 62/416,403 filed Nov. 2, 2016;
U.S. Prov. Ser. No. 62/443,769 filed Jan. 8, 2017;
U.S. Prov. Ser. No. 62/449,257 filed Jan. 23, 2017; and
U.S. Prov. Ser. No. 62/452,883 filed Jan. 31, 2017.
Said application U.S. Ser. No. 15/462,331 in turn is a continuation-in-part of and incorporates by reference each of the following applications:
U.S. Ser. No. 14/913,867 filed Feb. 23, 2016;
U.S. Ser. No. 15/371,858 filed Dec. 7, 2016;
International Patent Application No. PCT/US16/18670 filed Feb. 19, 2016; and
International Patent Application No. PCT/US16/65396 filed Dec. 7, 2016.
This patent application relates to the following provisional and non-provisional applications that are each incorporated by reference:
U.S. Prov. Ser. No. 62/119,521 filed Feb. 23, 2015;
U.S. Prov. Ser. No. 62/120,316 filed Feb. 24, 2015;
U.S. Prov. Ser. No. 62/139,754 filed Mar. 29, 2015;
U.S. Prov. Ser. No. 62/254,718 filed Nov. 13, 2015;
U.S. Prov. Ser. No. 62/259,991 filed Nov. 25, 2015;
U.S. Prov. Ser. No. 62/275,222 filed Jan. 5, 2016;
U.S. Prov. Ser. No. 62/275,241 filed Jan. 6, 2016;
U.S. Prov. Ser. No. 62/279,784 filed Jan. 17, 2016;
U.S. Prov. Ser. No. 62/287,901 filed Jan. 28, 2016; and
U.S. Prov. Ser. No. 62/299,453 filed Feb. 24, 2016.

FIELD

This patent specification generally relates mainly to a medical device for use in tissue examinations and endoscopic surgery such as in urology. More particularly, some embodiments relate to an integrated, handheld, low-cost surgical endoscope device having a single-use portion and a multiple-use portion.

BACKGROUND

Conventional endoscopy, or direct vision used to examine the interior of a hollow organ or cavity of the body, uses a complex lens system for transmitting the image from the distal tip of the endoscope to a viewer. The lens system is typically a relay lens system in the case of rigid endoscopes or a bundle of fiber optics or an objective lens system in the case of flexible endoscopes. In the case of both rigid and flexible conventional endoscopes, the lens or fiber optic system is relatively expensive and is intended to be re-used many times. Therefore, stringent decontamination and disinfection procedures need to be carried out after each use.

In surgical procedures where a needle is used to inject fluid such as a drug into the patient's tissues, a long injection needle is inserted into the working channel of the endoscope. In such procedures, it is common to use two or more operators to carry out the surgical procedure: one to operate the endoscope and another to operate the needle assembly and syringe. It is common for there to be a physical separation between display screen (e.g. mounted overhead), the endoscope (into the patient), and/or the syringe used to administer the drug. In such cases an operator or clinician has to look up the display screen and cannot simultaneously view the scope handle and the syringe. Furthermore, the separate needle assembly which is often long and somewhat cumbersome needs to be threaded through the working channel of the endoscope and substantial manual dexterity may be required to control the jabbing and injection process.

Disposable endoscopy is an emerging category of endoscopic instruments. In some cases the manufacture of endoscopes can be made inexpensive enough to be used on a single patient only. Disposable or single-use endoscopy lessens the risk of cross-contamination and hospital acquired diseases. Partially disposable endoscopy systems for hysteroscopy are discussed in U.S. Pat. No. 8,460,182, incorporated by reference herein. A hysteroscope having a disposable probe was offered by Endosee Corporation of Los Altos, Calif., and is now offered by CooperSurgical, Inc. of Trumbull, Conn., a company that acquired EndoSee Corporation.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

According to some embodiments that are particularly suitable for fields such as urology and endoscopic surgery rather than hysteroscopy, a low-cost surgical instrument for examining and injecting a desired fluid into a patient's tissue comprises an endoscope with a disposable distal portion and a reusable proximal portion, configured to enable a single user to operate the endoscope both (i) to visualize an internal region of the patient and (ii) to concurrently inject fluid in or adjacent said region through an injection needle permanently mounted at a distal part of the endoscope by jabbing with both portions. In this example, the endoscope comprises a handle configured to be grasped by the user's hand and having at least one button controlling endoscope functions, and an integral video display screen, wherein both the handle and the screen form a part of the reusable portion of the endoscope; a cannula forming a part of the disposable portion of the endoscope and configured with internal lumena and an injection needle permanently mounted at a distal part of the cannula for motion between a retracted position at which it is entirely within the cannula and a releasably locked protruding position in which it extends distally from the cannula; a connector at a proximal part of the disposable portion of the endoscope, configured to releasably mate tool-free with a connector at the reusable portion of the endoscope thereby releasably integrating the reusable and disposable portions; a needle actuation hub at the disposable portion of the endoscope, intermediate the connector of the disposable portion and the cannula; an actuation tab mounted to the hub and configured to be moved by the user's hand between a first position and a second position; said tab being coupled to the needle to drive it between its retracted and protruding positions as the user moves the tab between its first and second positions; an injection fluid port at the hub, said port being in fluid communication with the injection needle through the cannula so that fluid introduced in the port can be injected through the needle; and a light source and an imaging module with a video camera at a distal portion of the cannula, coupled with the screen to illuminate the region in the patient and provide images of the region to the screen under the control of said buttons on the handle. This configuration enables a single user holding the handle to use one hand to insert and retract the cannula in and from the patient, operate said buttons, move the needle from its retracted position to its protruded position, jab the needle into tissue, and retract the needle, and to use the same or the other hand to selectively force fluid into said fluid port.

In some embodiments, the endoscope further includes a source of fluid and a flexible conduit from the source to the injection fluid port, wherein the flexible conduit is the sole connection between the source of fluid and the endoscope, thereby helping to keep motion of the source of fluid from being mechanically transmitted to the reusable portion and/or the disposable portion of the endoscope at least while the needle is in its protruding position.

In some embodiments, the endoscope further includes a fluid source coupled with the fluid port via a conduit, and an attachment releasably securing the syringe to the handle to thereby enable the operator to use a single hand to operate the endoscope to visualize a region of the patient, to jab the needle into tissue, and to inject fluid into the tissue.

In some embodiments, the endoscope's video camera has a field of view (FOV) and the distal tip of the needle is at a central region of the FOV when the needle is in its protruding position.

In some embodiments, the endoscope's tab has a projection moving with the tab relative to the hub and the hub has stops configured to releasably engage the projection when the tab is in its first and second positions and thereby releasably lock the tab at least at the second tab position and thus the needle at its protruding position, and the hub further includes a hand-operated release button acting on said projection to thereby selectively release the tab and thus the needle from a locked position.

In some embodiments, the endoscope's hub is coupled to the mechanical connector of the disposable portion of the endoscope through an angularly sliding coupling enabling rotation of the cannula relative to the handle when the disposable and reusable portions are integrated.

In some embodiments, the endoscope's needle is no longer than the distance from the fluid port to the distal end of the cannula.

In some embodiments, the endoscope is free of openings at a distal part of the disposable portion for insertion of an injection needle.

In some embodiments, the connector of the disposable portion of the endoscope comprises a mechanical connector and an electrical connector spaced proximally from the mechanical connector, and said connector of the reusable portion comprises a mechanical connector configured to releasably mate tool-free with the mechanical connector of the disposable portion and an electrical connector spaced proximally from the distal end of the reusable portion and configured to releasably mate tool-free with the electrical connector of the disposable portion.

In some embodiments, the mechanical and electrical connectors of the disposable portion of the endoscope are male connectors and the electrical and mechanical connectors of the reusable portion and female connectors.

In some embodiments, the surgical instruments comprises: a disposable portion for a single use on a patient, comprising a cannula with an injection needle that is permanently mounted in the cannula for motion between a retracted position and a releasably locked protruded position; a reusable portion comprising a handle configured to be grasped by a user's hand; an electrical connector and a mechanical connector on each of the disposable portion and the reusable portion, said connectors releasably mating with each other to integrate the disposable portion and the reusable portion and to establish electrical connection between them; wherein each of electrical connectors is spaced in a proximal direction from each of the mechanical connectors thereby facilitating prevention of contamination of the electrical connectors from material in or on the disposable portion; a needle actuator tab mounted to the disposable portion and movable by hand between a retracted position and an extended position, said actuator being coupled with the needle to move the needle between its retracted and protruded positions as the tab moves between its retracted and extended position; an injection fluid port at the disposable portion, coupled with the injection needle for conveying thereto via the cannula fluid introduced into the port; an illumination source and an imaging module including a video camera mounted to a distal part of the cannula, a video screen mounted to the reusable part to move therewith and to rotate and/or tilt relative to the reusable part, and controls on the reusable portion to control video camera; and electrical connections between the reusable portion and the camera and illumination source to control the illumination source and the camera and to convey images from the camera for display on the screen. In this configuration, the endoscope, when integrated, is configured for selective operation with one hand to move the tab and the needle between their positions, to control the illumination source and camera, and to push the needle into tissue by jabbing at least the disposable portion when the needle is in its protruded position.

The endoscope can include a source of fluid and a flexible conduit connecting the fluid source to said fluid port in the disposable portion of the endoscope. The fluid source can be configured to be out of a mechanical connection with the reusable portions except through said flexible conduit, and can be located sufficiently close to the reusable portion for a single operator to operate the reusable portion with one hand and the fluid source with the other hand. In an alternative, the endoscope can be provided with an attachment mounting the fluid source to at least one of the reusable portion and the disposable portion for operation with a single hand of the endoscope enabling the user to utilize a single hand (i) to move the tab to thereby move the needle between its retracted and protruding positions, (ii) to operate said controls controlling the video camera, and (iii) to operate the fluid source to inject fluid therefrom through the needle. The fluid source can comprise a syringe, and the attachment can be secured to the handle and can include a syringe band into which the syringe can be slipped in and from which it can be slipped out. The attachment can further comprise a handle band secured to the handle, and projections on one of the band and depressions on the other for a releasable snap-fit of the bands to each other. As an alternative, the attachment can comprise hook-and-loop patches or bands secured to each of the fluid source and the handle and adapted to releasably couple with each other thereby attaching the fluid source to the handle.

In some embodiments, the video screen is mounted to the handle for rotation or tilting about two axes that are transverse to each other so it can be rotated or tilted relative to the handle to facilitate selection of the screen orientation relative to the user before or during a patient procedure. The endoscope can further include a flushing fluid port that is spaced in the distal direction from the injection fluid port, and the cannula can include at least one flushing fluid opening at a distal part of the camera and at least one lumen connecting the flushing fluid port with the at least one flushing fluid opening. The video camera can have a field of view and the needle, when in its protruding position, can have a tip that is at a central position in said field of view. The needle actuator tab can be mounted to the hub for back-and-forth motion in the proximal-distal direction. The needle when in its retracted position can be entirely within the cannula.

In some embodiments, the video camera at the tip of the cannula is a digital camera or camera module using on-chip or on-module conversion of analog-to-digital image information so that the video signal sent from the camera toward the image display module is a digital signal. Numerous benefits flow from the use of such a digital camera or camera module. The signal line is less prone to interference because it is digital. In some embodiments, the cannula tip diameter is 5 mm or less, and the diameter (or the largest dimension across the length of the cannula) of the video camera module in the cannula tip is less, such as in the range of 2 mm mm to 4 mm mm, and preferably 3 mm or less.

In some embodiments, two or more cannulas that are otherwise the same but differ in length can be provided so that a shorter cannula can be used for applications such as examining bladders of female patients and a longer cannula can be used for examining bladders of male patients. For example, the shorter cannula can have a working length of 9 inches or less, or 8 inches or less, and the longer cannula can have a working length of 13 inches or more. In cases where the available shorter cannula is not long enough for a female patient, a longer example of the cannula can be used.

In some embodiments, the cannula is used for placing a guide wire to the interior of the bladder. The guide wire can pass through one of the lumens in the cannula, for example a fluid lumen, or an additional lumen can be provided for the guide wire or the wire can be integrated in or on the cannula wall.

A method of using the surgical instrument can comprise: removing a disposable distal portion of an endoscope from sterile packaging and releasably attaching it tool-free to a reusable portion of the endoscope to thereby assemble the endoscope; introducing a cannula that is a part of the distal portion of the endoscope into a patient until a tip of the cannula reaches a selected region in the patient; illuminating the selected region with a light source mounted in the tip of the cannula and visualizing the region with a video camera mounted in the cannula tip and supplying images to a video screen mounted to the reusable portion of the endoscope; operating a tab movably mounted to the reusable portion of the endoscope to thereby move an injection needle that is permanently mounted to the cannula tip from a retracted position in which the needle is entirely within the cannula to a releasably locked protruding position in which the needle protrudes from the cannula; jabbing the needle into tissue by moving the reusable and disposable portions as a unit while the needle is in its protruding position; and injecting fluid through the needle from a fluid source that is connected to the endoscope; retracting the needle to its retracted position by operating the tab and withdrawing the cannula from the patient. A single user can operates the endoscope to introduce the cannula into the patient, visualize the region, jab the needle, inject fluid through the needle, and retract the needle and withdraw the cannula from the patient, using one or both hands. The method can include detaching the disposable portion from the reusable portion by hand, tool-free, and disposing of the disposable portion.

In some embodiments of the method, the user can use a single hand to operate the endoscope to visualize the region, jab the needle, inject fluid through the needle, and retract the needle. In some embodiments, the method further includes attaching a syringe to the handle in a position in which the same user's hand operating controls of the camera on the handle reaches the syringe plunger to inject fluid from the syringe through the needle and into the patient.

As used herein, the grammatical conjunctions "and", "or" and "and/or" are all intended to indicate that one or more of the cases, object or subjects they connect may occur or be present. In this way, as used herein the term "or" in all cases indicates an "inclusive or" meaning rather than an "exclusive or" meaning.

As used herein the terms "surgical" or "surgery" refer to any physical intervention on a patient's tissues, and does not necessarily involve cutting a patient's tissues or closure of a previously sustained wound.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIGS. 4A, 4B and 4C are a side view, perspective view and cross section of a cannula used on a handheld surgical endoscope, according to some embodiments;

DETAILED DESCRIPTION

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

Figure 1:
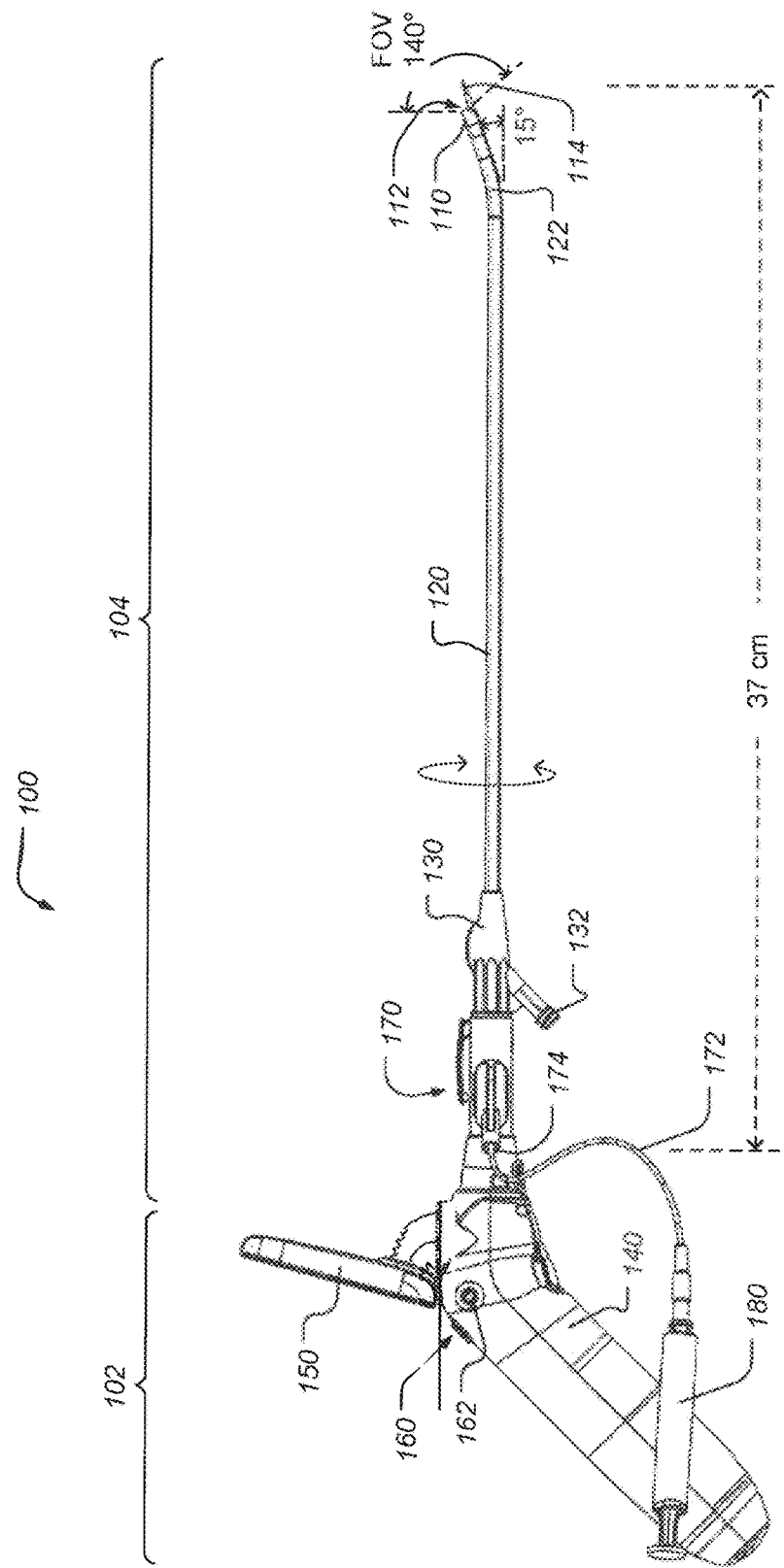
FIGS. 1 and 2 are a right side view and a top view, respectively, of a handheld surgical endoscope, according to some embodiments.
Figure 2:
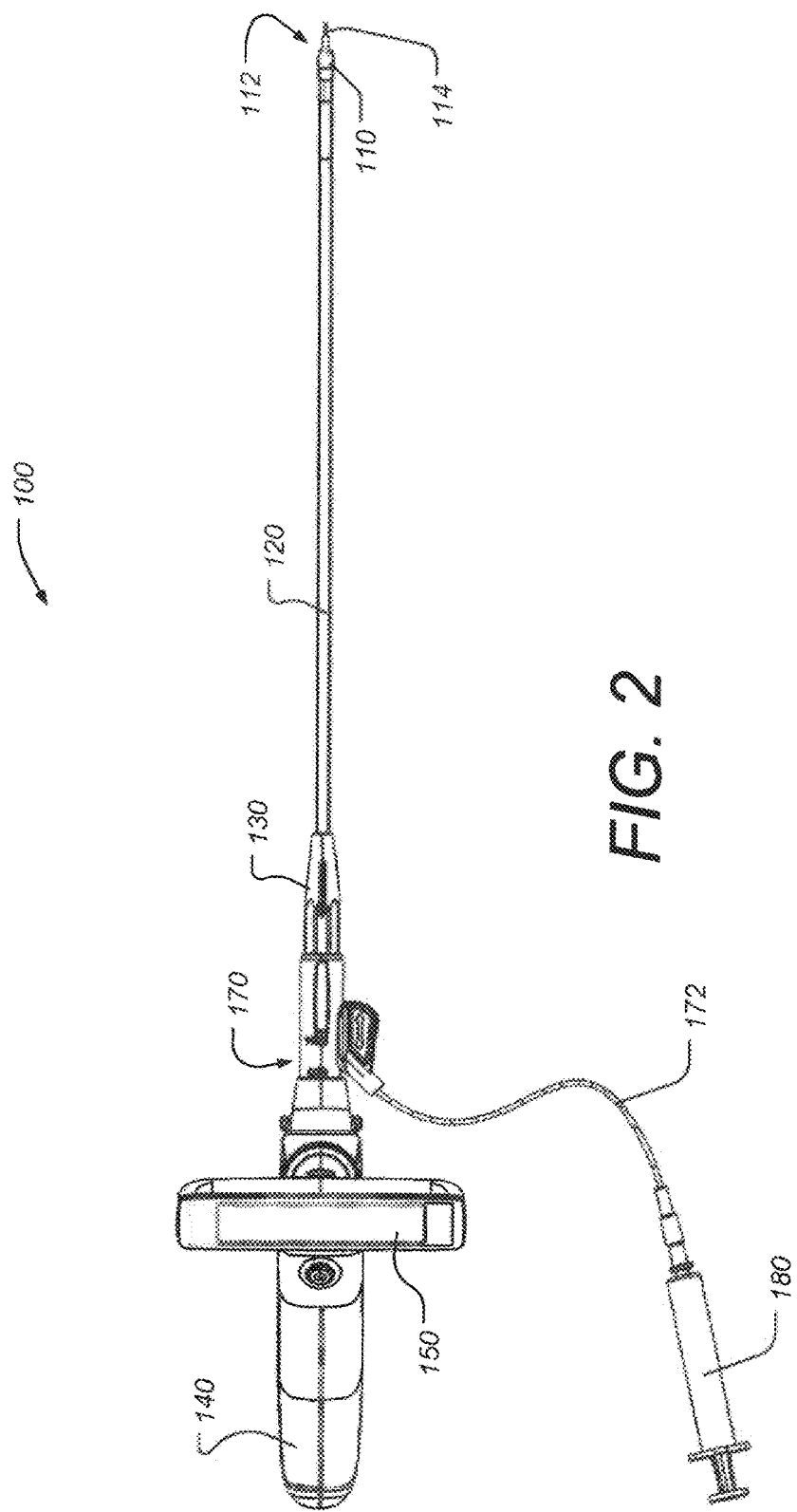

FIGS. 1 and 2 are a right side view and a top view, respectively, of a handheld surgical endoscope, according to some embodiments. The surgical endoscope 100 includes an elongated cannula 120 with a distal tip 112 for inserting into a hollow organ or cavity of the body. A needle 114 passes trough a dedicated lumen in cannula 120. The tip of needle 114 can be extended to protrude distally from distal tip 112 as shown. The needle 114 is hollow and at needle actuation hub 170 is in fluid communication with fluid line 172, which in turn is connected to syringe 180 (or other fluid dispensing device).

According to some embodiments, a separate tip sub-assembly 110 is attached to the cannula 120 which can be made from an extruded material. For further details relating to a separate tip sub-assembly for a handheld endoscope, see co-pending U.S. patent application Ser. No. 15/371,858 filed Dec. 7, 2016, referred to hereinafter as "the co-pending '858 application." Sub-assembly 110 includes an imaging module and one or more LED light sources for viewing the organ or cavity into which it is inserted. The tip assembly 110 also includes one or more fluid ports. The distal end of the cannula 120 can also be slightly bent as shown in bent region 122. According to some embodiments, a bend of about 15 degrees in region 122 has been found to be suitable for many applications, but using other angles in alternative embodiments is not excluded.

According to some embodiments, the cannula 120 includes one or more fluid channels which are fluidly connected to distal fluid port 132 at fluid hub and connection assembly 130. Port 132 includes a Luer fitting to facilitate leak-free connection of port 132 with various medical fluid components. The fluid channels or lumens in cannula 120 are also connected to a distal facing fluid ports (orifice or ports 616 and 618 shown in FIGS. 6A, and 6B) of tip assembly 110. According to some embodiments, wires running from the LED light sources and camera module in tip assembly 110 pass through a separate channel in cannula 120.

The endoscope 100 includes a handle portion 140 that is sized and shaped in a pistol-like fashion for easy grasping by the endoscope operator (e.g. doctor or other medical professional). A display module 150 is rotatably mounted on handle 140 via a bearing which can be a plain bearing made of plastic, and a rubber coated hinge. Also visible on handle 140 are image capture button 160 and power button 162. According to some embodiments handle 140 and display module 150 are configured to be re-usable and make up reusable portion 102. According to some embodiments, handle 140 is similar or identical to handle 140 shown and described in the co-pending '858 application.

Single-use portion 104 includes the needle actuation hub 170, fluid hub and connection assembly 130, cannula 120 and tip assembly 110. Single-use portion 104 is made at a relatively low-cost and is intended to be disposed of after a single-use. By making the tip, cannula, fluid hub all single-use, stringent decontamination and disinfection procedures as well as the risk of cross-contamination and hospital acquired diseases can be significantly lessened or avoided. According to some embodiments the disposable, single-use portion (portion 104 shown in FIGS. 1 and 3) is sterilized, for example, during production and is provided to the user in a sealed sterilized pouch, for ease of storage and handling. The camera module in the tip assembly can have a wide angle of view, such as 140 degrees in this example. According to some embodiments, the fluid line 172 is also included in single use portion 104 and can be attached to hub 170 and included in the same sterilized pouch.

According to some embodiments, the length of needle 114, including the fluid pathway within needle actuation hub 170 (i.e. from the distal tip of needle 114 to the needle fluid port 174 is less than 50 cm, and according to some embodiments is about 37 cm. This is contrast to surgical procedures carried out with a conventional endoscope having a working channel through which is passed a separate needle assembly. In those cases the separate needle assembly is operated by a second clinician which necessitates a longer needle (e.g. between 70 cm to 100 cm) to allow for enough working space for each clinician. Using a much shorter needle, according to the embodiments described herein, allows for less wasted drug fluid remaining within the needle.

According to some embodiments, the surgical endoscope is configured to allow cannula 120 to rotate about its longitudinal axis as shown by the dotted arrow in FIG. 1. For further details of how to configure the hub 130 to allow rotation of the cannula, see the co-pending '858 application. According to some embodiments, the cannula rotation can include a certain amount of friction (e.g. friction overcome by torque in the range of 0.04 N·m to 0.2 N·m). This allows for a "rotate and hold" of the cannula that is desirable for some procedures. For further details of how to configure such a "frictional fit," see the co-pending '858 application. According to some embodiments, the endoscope can be configured to detect the rotational position of the cannula 120 relative to the handle 140. The detected rotational position is then input to a software algorithm configured to reorient the image displayed on display module 150 such that a correctly oriented image is displayed to the operator. For further details of such rotational position detection, see the co-pending '858 application.

Figure 3:
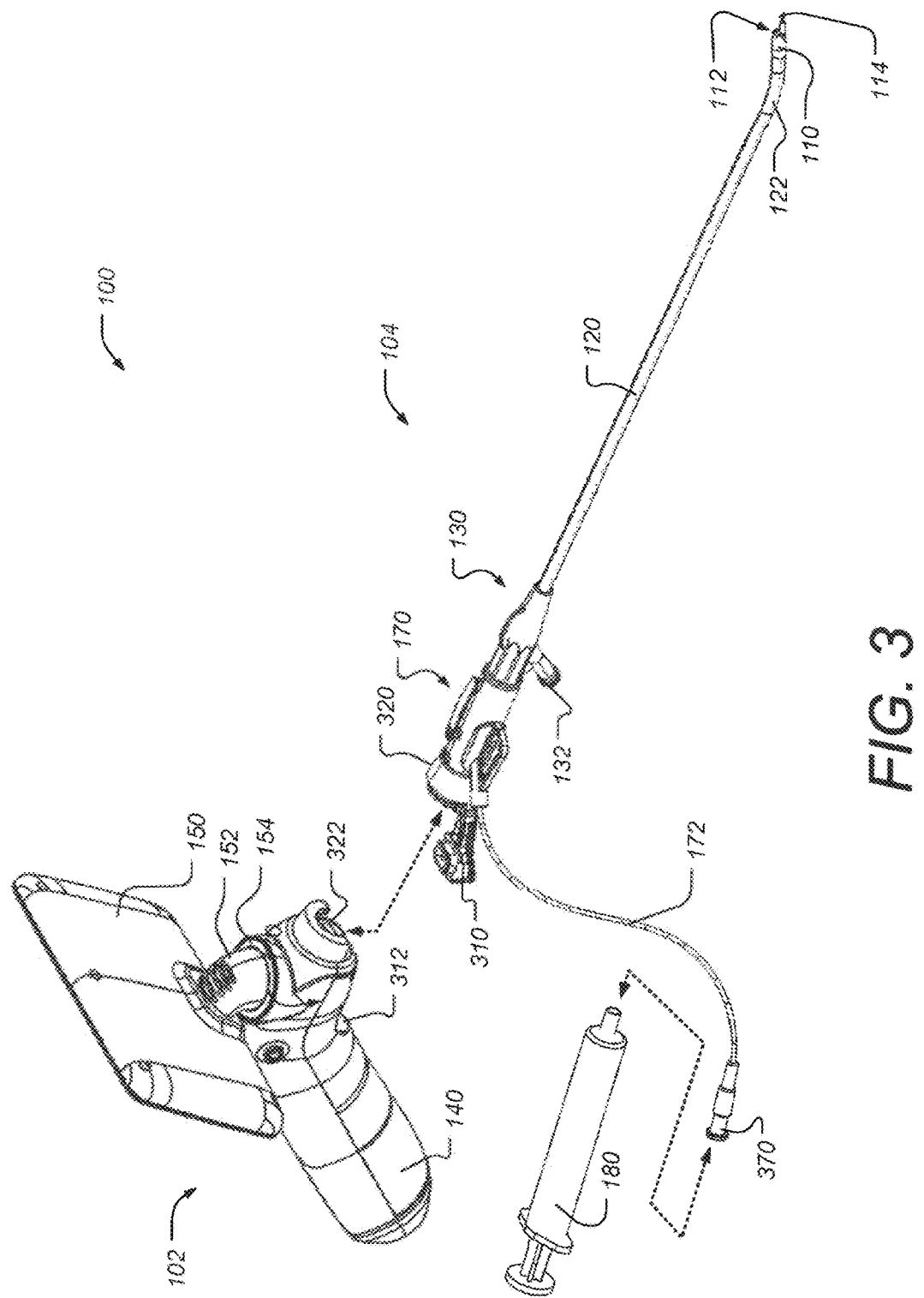
FIG. 3 is perspective view showing aspects of attachment and detachment of single-use and reusable portions of a handheld surgical endoscope, according to some embodiments.

FIG. 3 is perspective view showing aspects of attachment and detachment of single-use and reusable portions of a handheld surgical endoscope, according to some embodiments. The single-use portion 104 and reusable portion 102 attach mechanically primarily via mating mechanical connectors 320 and 322. Electrical connection is made via separate mating electrical connectors 310 and 312. In this example the two portions 102 and 104 are attached via translation vertically towards each other. Note that the electrical connector 310 and mechanical connector 320 are both separated from the fluid hub 130 and from needle actuation hub 170. This separation allows for easy and effective fluid sealing to prevent fluid from hubs 170 and 130 from penetrating internally towards connectors 310 and 320 and also allows some protection against any exterior fluid, for example from fluid port 132 from reaching and possibly compromising electrical connectors 310 and 312. Also, the separation between mechanical connector 320 and hub 130 allows for a sleeve bearing to allow for rotating of cannula 120 relative to the proximal portion of hub 130. For further details of this rotation mechanism, see the co-pending '858 application, for example FIGS. 8A-8C and 9A-9B and associated text of the co-pending '858 application. The physical separation of the fluid hub 130 and the mechanical and electrical connectors 320 and 310 also provide additional assurance against accidental contamination from fluid hub 130 to the re-usable portion 102. For further details regarding the physical separation and associated benefits, see the co-pending '858 application.

FIGS. 4A, 4B and 4C are a side view, perspective view and cross section of a cannula used on a handheld surgical endoscope, according to some embodiments. The cannula 120 can be extruded and made of a nylon material such as nylon 12 (e.g. Grilamid® L25). The distal end of cannula 120 can include a bent region 122 which is beneficial for certain applications and can effectively increase the field of view of the camera fixed to the distal tip when the endoscope is rotated about its central longitudinal axis. FIGS. 4B and 4C show a further detail of the internal lumina of cannula 120. An insulated electrical cable (not shown) is run though the upper lumen 430. For further details of the insulated cable, which includes conductors used for sending power to the camera and LEDs in the distal tip and signals back to electronics in the handle, see the co-pending '858 application. Fluid lumina 416 and 418 are used to carry fluid between fluid port 132 (shown in FIGS. 1-3) and the distal fluid ports (see ports 616 and 618 shown in FIG. 6A). In this example, lumina 416 and 418 each have a cross sectional area of about 1.33 mm$^2$. The needle 114 (shown in FIGS. 1-3, 6A-B and 8A-B) passes through lumen 470. Dimensions are shown in FIG. 4C for an example device. In general, the lumen 470 should be dimensioned to allow passage of the needle 114 which according to some embodiments is between 26 gauge (0.4636 mm) and 21 gauge (0.8192 mm). According to some embodiments the needle 114 is 23 gauge (0.6414 mm) or 22 gauge (0.7176 mm). According to some embodiments, the cannula 120 can be made such that its stiffness is not constant along its length. For example, it may be useful in some clinical applications to provide a cannula that is more flexible towards the distal tip and stiffer towards the handle. In such cases the cannula 120 can be made from a multi-durometer tubing such as a multi-duro Pebax® or Grilamid®.

According to some embodiments, cannula 120 is rotatable relative to the handle. The rotation mechanism can be provided in hub 130 and further details are shown and described in the co-pending '858 application.

Figure 5A:
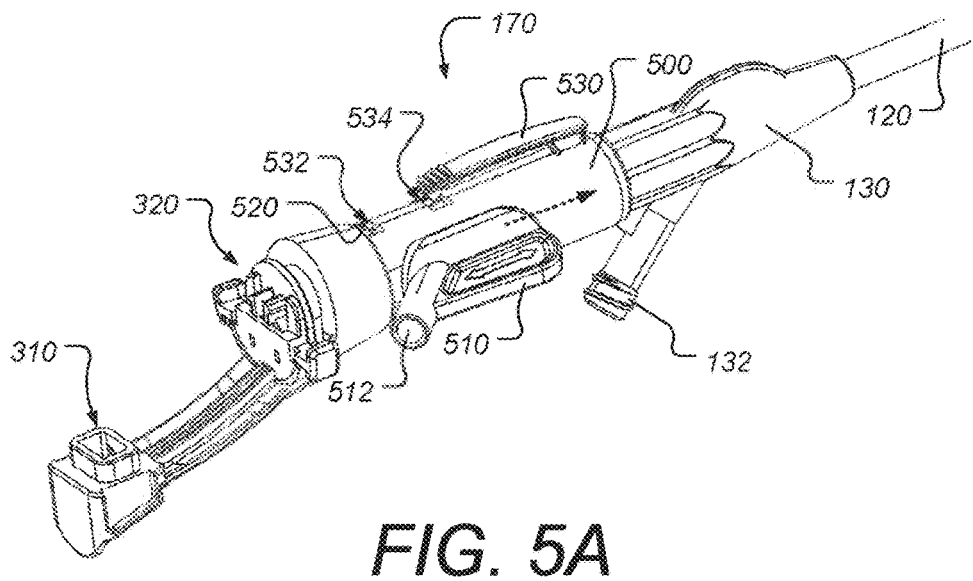
FIGS. 5A and 5B are perspective views showing aspects of needle actuation for a handheld surgical endoscope, according to some embodiments.
Figure 5B:
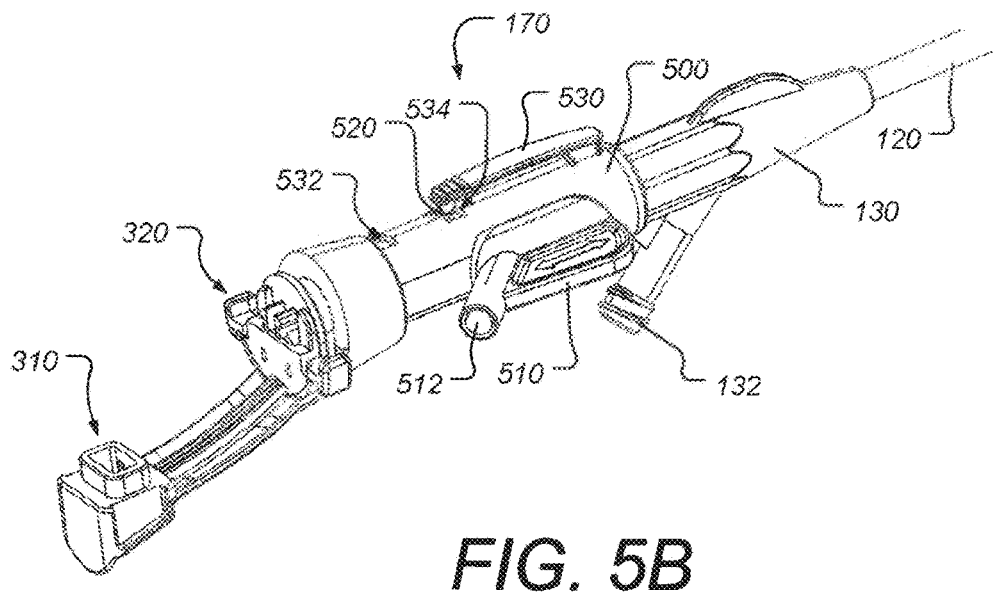

FIGS. 5A and 5B are perspective views showing aspects of needle actuation for a handheld surgical endoscope, according to some embodiments. FIG. 5A shows the needle actuation hub 170 when the needle is in the retracted position while FIG. 5B shows the hub 170 when the needle is in the extended position. Hub 170 includes an outer housing 500 through which are formed two windows, proximal window 532 and distal window 534. A lock release button 530 extends from the housing 500 and includes a inwardly protruding tab that aligns with distal window 534. Actuation tab 510 is moveable relative to the hub housing 500. Moving with tab 510 is fluid port 512 that is in fluid communication with fluid line 172 (not shown), spring tab 520 and needle 114 (not shown). Further detail of the movable portions of hub 170 is shown in FIG. 7B.

Figure 6A:
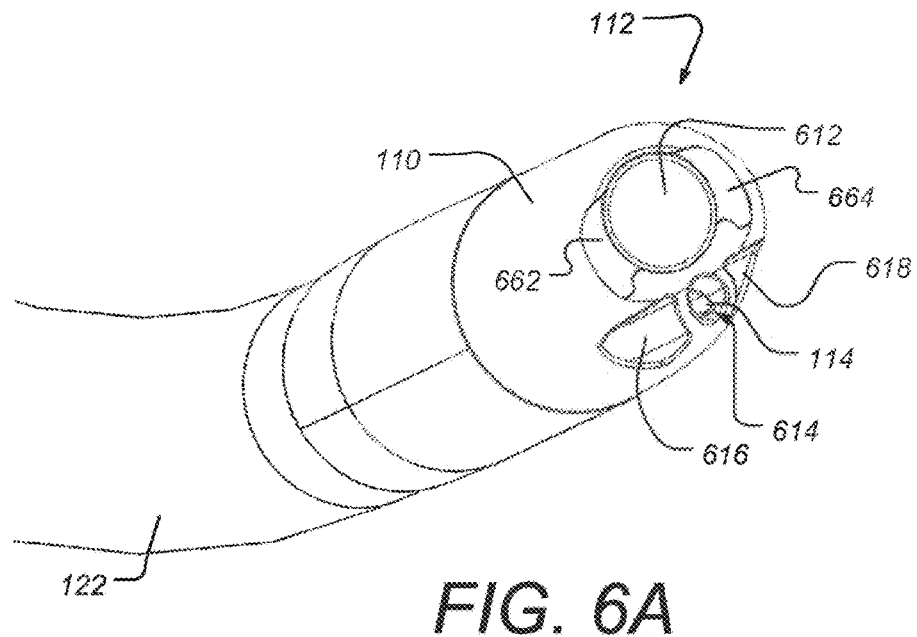
FIGS. 6A and 6B are perspective views of distal tip 112 and show aspects of the needle actuation, according to some embodiments.
Figure 6B:
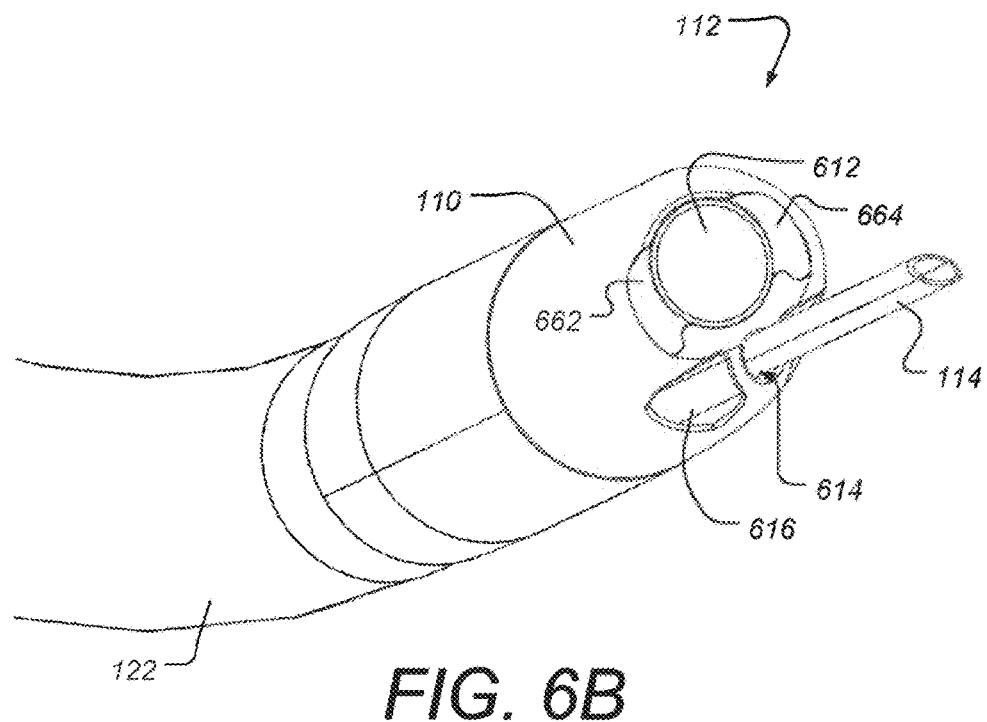

FIGS. 6A and 6B are perspective views of distal tip 112 and show aspects of the needle actuation, according to some embodiments. FIG. 6A shows tip 112 when the needle 114 in the retracted position while FIG. 6B shows tip 112 when the needle 114 is in the extended position. Note that while in the retracted position, the sharp tip of needle 114 is fully recessed within needle port 614 of tip assembly 110 and there is no risk of a sharps injury from the tip of needle 114. Also visible in FIGS. 6A and 6B are camera lens dust cover 612, two light-guide lenses 662 and 664 (for LED light sources) and distal fluid ports 616 and 618. The distal fluid ports 616 and 618 are provided to allow for fluid communication with fluid lumina 410 and 412 of cannula 120 (shown in FIGS. 4B and 4C). In this example, each of the fluid ports 616 and 618 have a cross sectional area of about 1.6 mm$^2$. Note that port 132, lumina 410 and 412 and distal fluid ports 616 and 618 can be configured to provide fluid in-flow (i.e. flowing fluid out of the endoscope and into the patients organ or cavity and/or fluid out-flow (i.e. flowing fluid out of the patient's organ or cavity and into the endoscope).

Figure 7A:
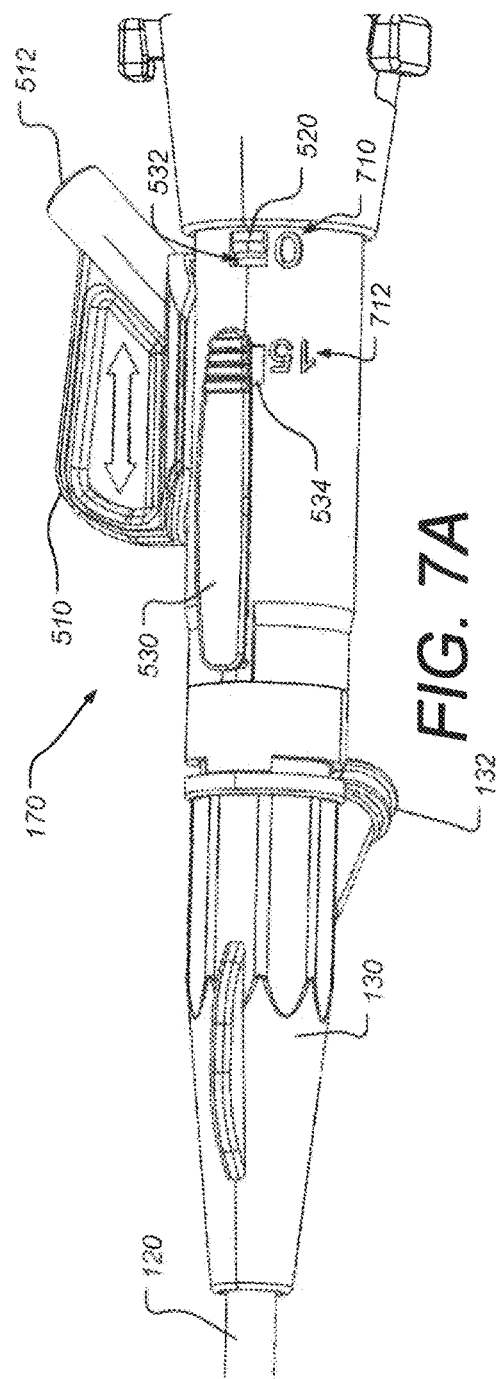
FIGS. 7A and 7B are perspective views of parts of the single use portion of handheld surgical endoscope, according to some embodiments.
Figure 7B:
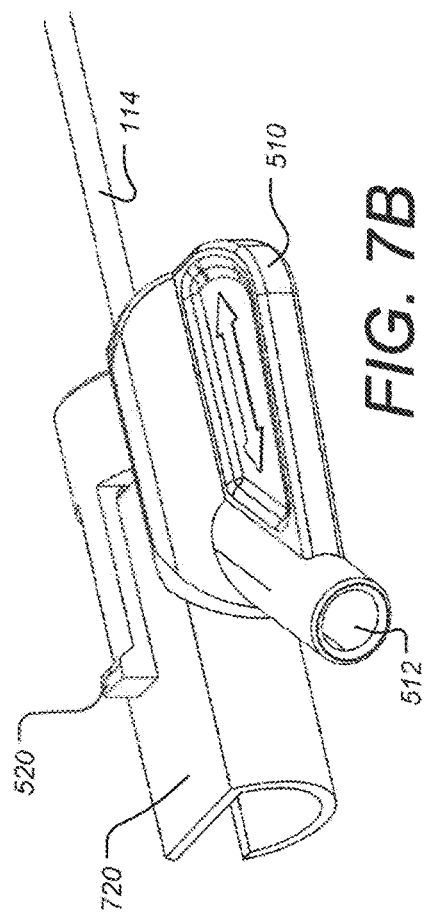

FIGS. 7A and 7B are perspective views of parts of the single use portion of handheld surgical endoscope, according to some embodiments. FIG. 7A shows the needle actuation hub 170 from another perspective in which the needle extension markings 710 and 712 are visible. In this example, marking 710 is a "0" indicating to the operator that the needle is fully retracted when spring tab 520 protrudes through proximal window 532, and marking 712 is a "15" indicating that the needle is extended by 15 mm when tab 520 protrudes through distal window 534. According to some embodiments, the full extension of the needle can be amounts other than 15 mm (such as values between 10 and 20 mm) and the marking 712 will reflect that value. FIG. 7B shows carrier 720 which is fixedly attached to actuation tab 510, spring tab 510 and needle 114. According to some embodiments carrier 720, spring tab 520 and/or actuation tab 510 are molded from a single piece of polymer material. As shown, spring tab 520 has ramp shaped distal edge and square shaped proximal edge. This shape allows for it move freely distally but will "lock" when it reaches full extension and protrudes through the distal window of housing 500. Needle 114 is glued or bonded into an opening of carrier 720. A fluid-tight pathway is provided through carrier 720 between fluid port 512 and the inner lumen of needle 114.

Referring to FIG. 5A, the actuation tab 510 is shown in the retracted position where tab 510 it is in its most rearward or proximal position relative to the hub housing 500. In this position, spring tab 520 protrudes through proximal window 532 of housing 500 and the tip of needle 114 is recessed within the needle port 614 as shown in FIG. 6A. In order to extend the tip of needle 114 so as to penetrate a patient's tissue, the operator moves actuation tab 510 forward (distally) relative to the housing 500 as shown by the dotted arrow in FIG. 5A. This causes the carrier 720 (shown in FIG. 7B) to move distally relative to the housing 500, and needle 114 to translate distally within lumen 470 (shown in FIGS. 4B and 4c) of cannula 120 and distally relative to tip assembly 110. As shown in FIG. 7B, spring tab 520 is movable radially and has ramp shape distal edge and square shaped proximal edge. Therefore the spring tab 520 is pushed inwards radially by the proximal edge of the proximal window 532. As the actuation tab 510 is pushed further distally, the top surface of tab 520 moves across the inner surface of housing 500 and towards distal window 534. When the spring tab 520 reaches the distal window 534 the radial spring force pushes the tip of tab 520 through the distal window 534. The square shaped proximal edge of spring tab 520 engages the square shaped proximal edge of window 534 which effectively "locks" or prevents retraction or proximal movement of needle 114, carrier 720 and actuation tab 510. This locking mechanism is useful when using the needle to inject the desired fluid (such as a drug) into the patient's tissue since the entire endoscope can be used to push the needle without the needle retracting back into the cannula. The surgical endoscope with its needle in a fully extended state is depicted in FIGS. 5B and 6B.

When the operator wishes to retract the needle, the lock release button 530 is depressed which forces the spring tab 520 inwards though the window 534. In the depressed state, the spring tab 520 is no longer "locked" by the distal window 534 and the actuation tab 510 can then be moved rearwards or proximally relative to the housing 500 which caused the needle to retract back within the tip assembly 110 such as shown in FIG. 6A. According to some embodiments, the spring tab 520 can be shaped with square edges on both proximal and distal sides which will allow for the needle to be releasably locked in both the retracted and protruding positions. In such cases the lock release button 530 is used to unlock the tab 520 in either position to allow actuation of the needle.

Figure 8A:
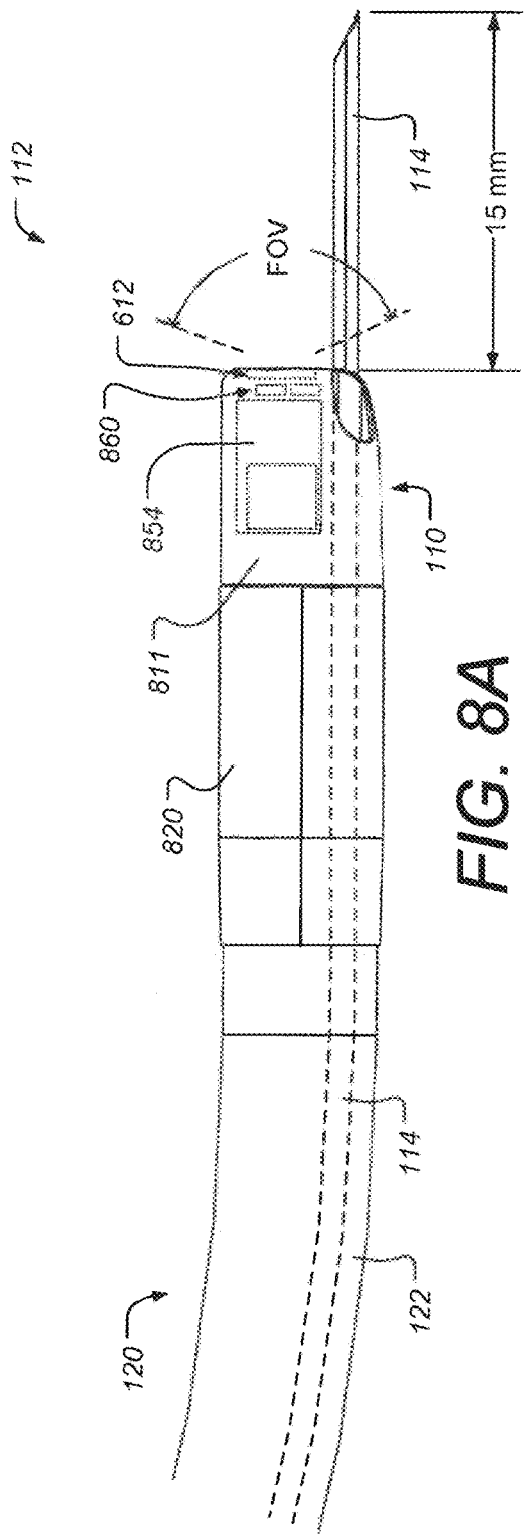
FIGS. 8A and 8B are side and cross section views of the distal tip of a handheld surgical endoscope, according to some embodiments.
Figure 8B:
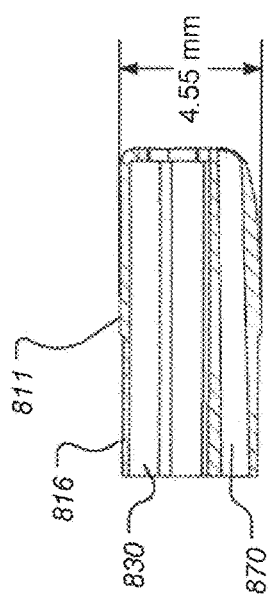

FIGS. 8A and 8B are side and cross section views of the distal tip of a handheld surgical endoscope, according to some embodiments. The cannula 120 and housing 811 of cannula tip 110 are held together using a sleeve 820 that is dimensioned to fit around both the outer surface of the distal end of cannula 120 and the proximal end 816 of tip housing 811. Tip housing 811 includes an upper cavity 830 which houses the camera assembly 854 and LEDs 860. As separate needle cavity 870 is included in tip housing 811 to allow passage of the needle 114. In the example shown the needle 114 protrudes 15 mm when fully extended, which has been found to be suitable extension amount for many surgical urology applications. According to some other embodiments, other extension amounts such as between 10 and 20 mm can be implemented. According to some embodiments, the needle 114 is not parallel to the center axis of the distal tip assembly 110 and housing 811. Rather the needle 114 is angled at about 2~5 degrees upwards (towards the camera), so that when the needle 114 is in fully protruded position (by 10~20 mm, preferably by 15 mm), its distal tip will roughly reach the center of the FOV of the camera. This can be accomplished by appropriate shaping of the needle cavity 870 in housing 811. According to some embodiments, sleeve 820 is made of stainless steel, although other material can be used. The three pieces, cannula 120, sleeve 820 and tip housing 811 can be glued together using, for example, a U-V cured bonding glue. For further details of the tip assembly 110 including suitable sensor, lens and LED components, as well as suitable assembly and bonding techniques, see the co-pending '858 application. According to some embodiments, the field of view (FOV) of the camera is configured such that when extended the tip of needle 114 is plainly and clearly visible by the sensor and can be displayed as such to the operator. According to some embodiments, the maximum outer diameter of the tip housing 811 is about 15 fr (or 5 mm) or less, and the other diameter of the cannula 120 is about 4.8 mm or less. This is in contrast to conventional rigid endoscopes which often have a outer diameter of about 7 mm. According to some embodiments, the distal outer edge of tip housing 811 is rounded to facilitate insertion in/though tissue passages and alleviate tissue contact issues. For further details of suitable rounding dimensions and criteria see the co-pending '858 application.

Figure 9:
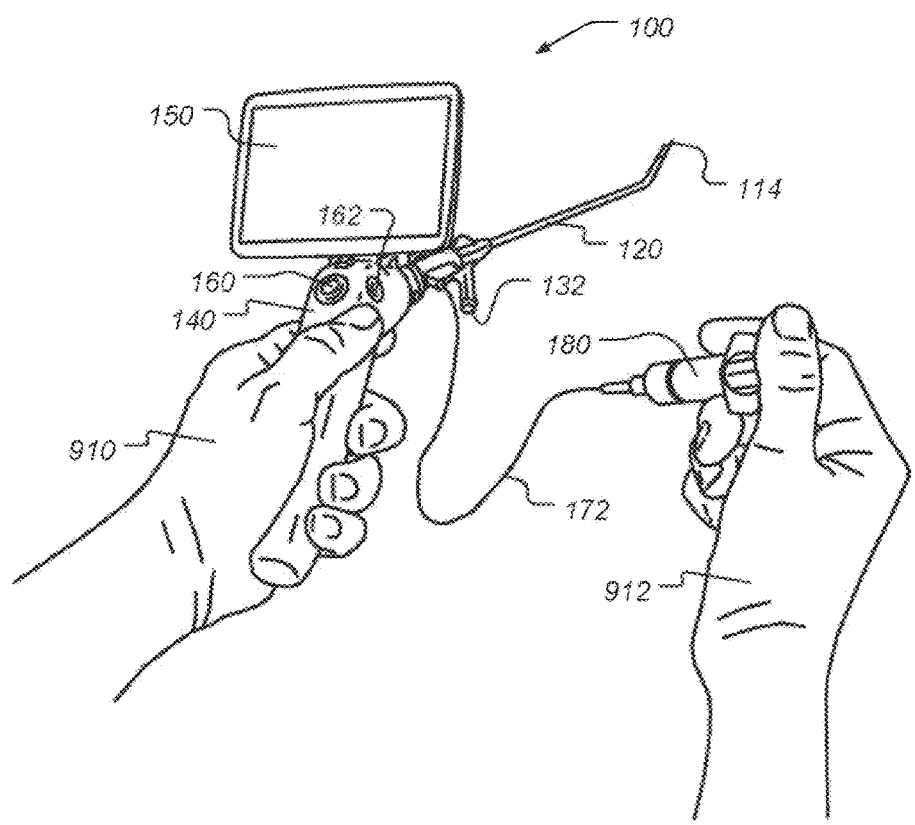
FIG. 9 is a perspective view of a handheld surgical endoscope being used to perform a surgical procedure by a single operator, according to some embodiments.

FIG. 9 is a perspective view of a handheld surgical endoscope being used to perform a surgical procedure by a single operator, according to some embodiments. Unlike conventional endoscopic surgical procedures that are performed using at least two skilled operators or clinicians, according to some embodiments, the surgical endoscope 100 with an integrated needle are configured for a single operator to perform many surgical procedures. Shown in FIG. 9 is a single operator, with his/her left hand 910 grasping the handle 140 (and optionally press the image capture button 160) and his/her right hand 912 operating the syringe 180 to dispense the drug (or other fluid) via the extended needle 114. Note that the patient and patient's tissues are not shown for purposes of clarity. By integrating the needle assembly with the handheld endoscope with attached display as shown and described herein, it has been found that a single operator can both control endoscope and perform the jabbing with the needle (using the entire endoscope) and administer the drug fluid in the syringe. Although the FIG. 9 is shown with the left hand operating handle of endoscope 100 and right hand operating the syringe, the operator could easily perform the procedure with his/her hands switched if desired (i.e. right hand operating the handle and left hand operating the syringe.

Figure 10A:
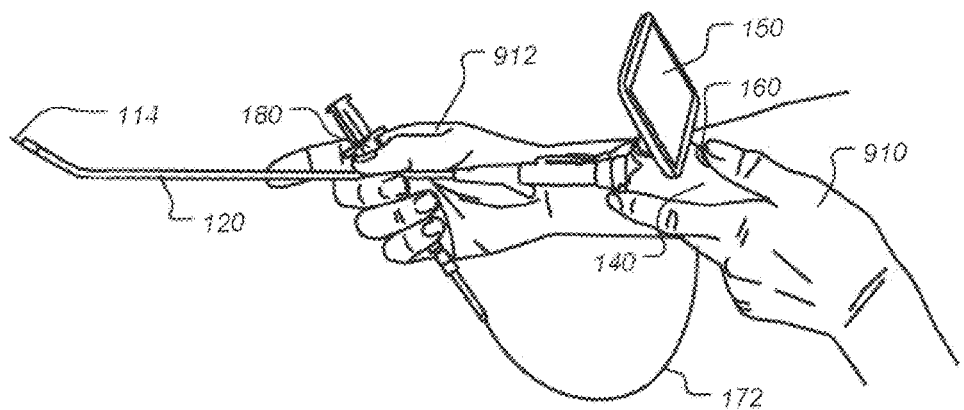
FIGS. 10A and 10B are further perspective views of a handheld surgical endoscope being used to perform a surgical procedure by a single operator, according to some embodiments.
Figure 10B:
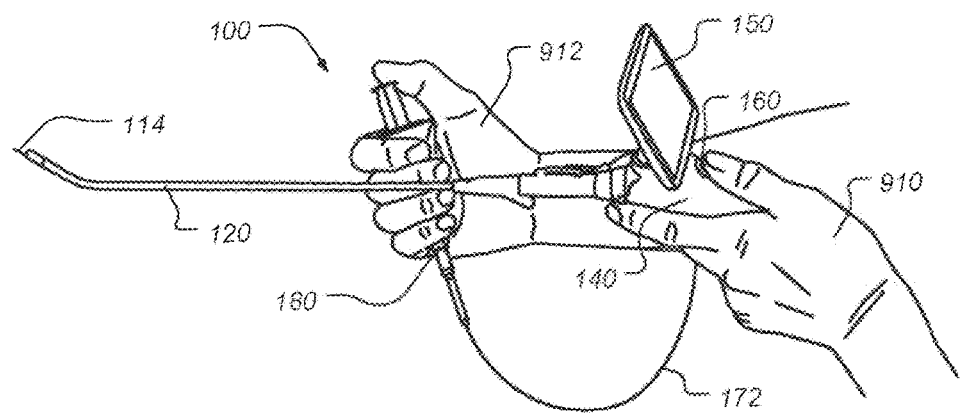

FIGS. 10A and 10B are further perspective views of a handheld surgical endoscope being used to perform a surgical procedure by a single operator, according to some embodiments. It has been found that for some procedures, an operator may prefer to manipulate the cannula 120 with one hand while using the other hand to grasp the handle. FIGS. 10A and 10B illustrate how this can be performed by a single operator to both manipulate the endoscope and control the syringe for administering the drug. In particular, the operator uses his/her left hand 910 to grasp the handle and optionally press the capture button 160, and his/her right hand 912 to manipulate the cannula 120 (shown in FIG. 10A) and administer the drug from syringe 180 (shown in FIG. 10B).

Figure 11:
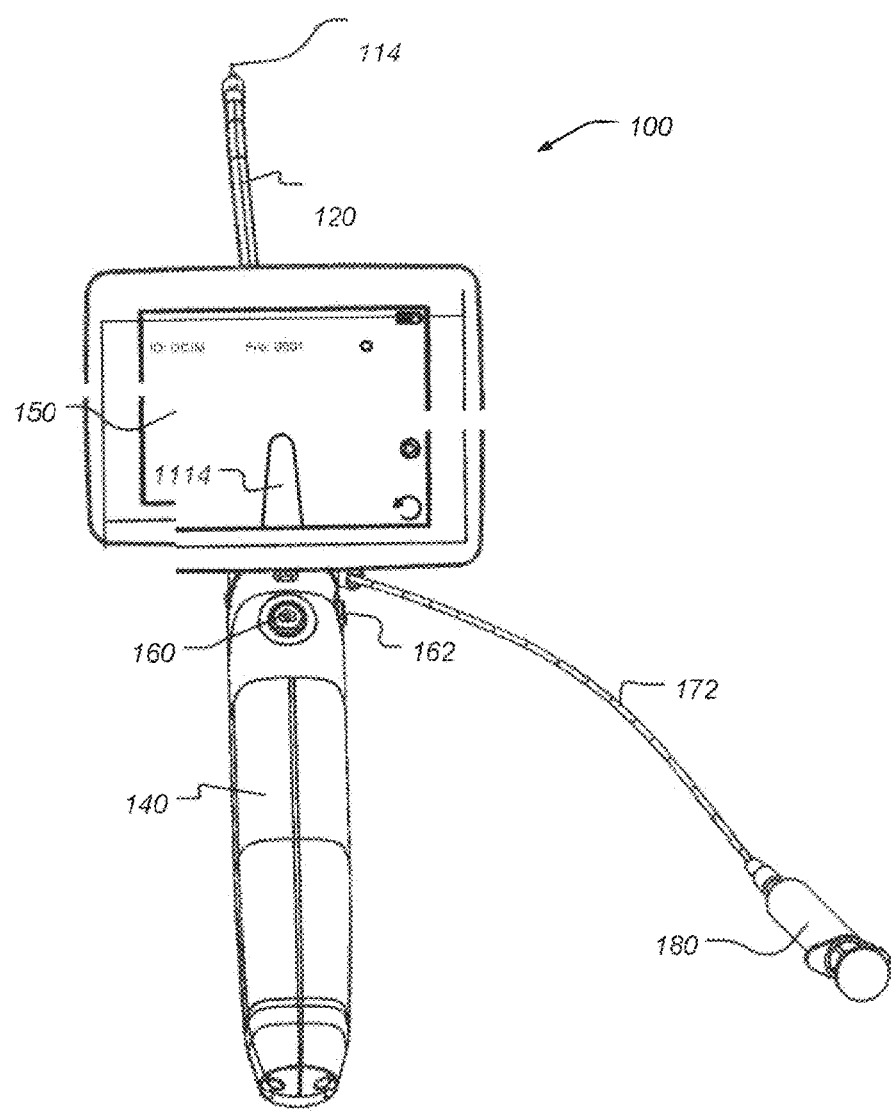
FIG. 11 is a perspective view of a handheld surgical endoscope, according to some embodiments.

FIG. 11 is a perspective view of a handheld surgical endoscope, according to some embodiments. As shown, when needle 114 is in the extended position, the camera sensor captures the needle tip and the display 150 show the needle tip 1115 clearly in the central portion of the display screen. As is also apparent in FIG. 11, the handheld surgical endoscope 100 is ergonomically configured to a single operator to view the endoscope, the display screen and the syringe, which further facilitates carrying out surgical procedures with a single operator.

Figure 12:
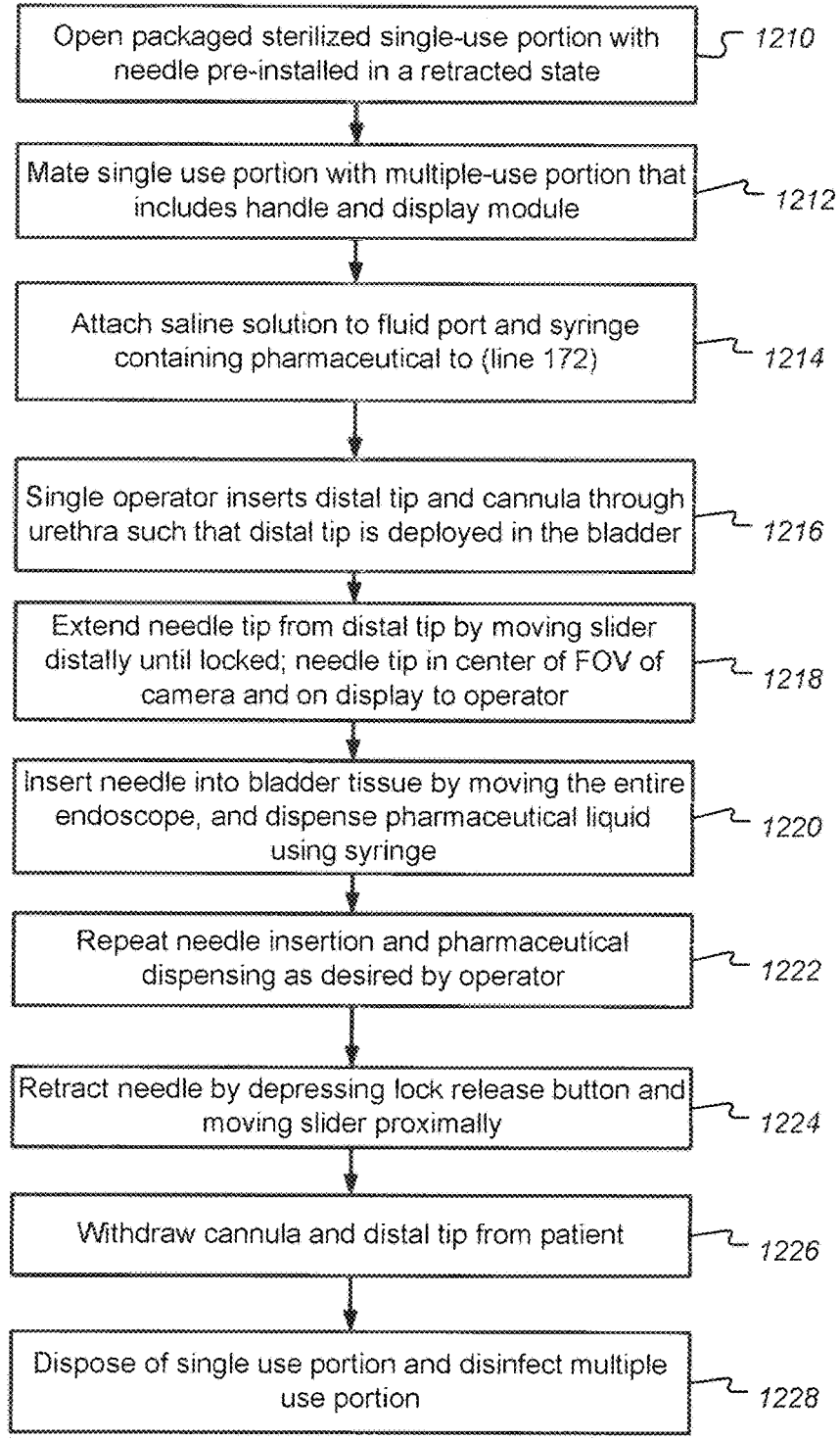
FIG. 12 is a block diagram showing aspects of single operator carrying out a surgical procedure with a handheld surgical endoscope, according to some embodiments.

FIG. 12 is a block diagram showing aspects of single operator carrying out a surgical procedure with a handheld surgical endoscope, according to some embodiments. In block 1210, the sterilized packaging containing the single use portion of the endoscope is opened. As shown in FIGS. 1-3, the single use portion 104 includes the fluid hub 130, cannula 120, tip assembly 110, the needle actuation hub 170 and fluid line 172. The needle 114 is pre-installed in a dedicated lumen in cannula 120 in the recessed (not-extended) position so as to reduce risk of a sharps injury. In block 1212, the single use portion from the sterilized package is mated with the multiple use portion. As shown in FIGS. 1-3, the multiple use portion 102 includes the handle 140 and the display module 150. In block 1214 a saline solution supply, such as from a syringe is attached to fluid port 132, and the syringe 180 containing the pharmaceutical is connected to fluid line 172.

In block 1216, a single operator inserts the distal tip 112 and cannula 120 through the patient's urethra such that the distal tip 112 is deployed in the patient's bladder. Note that the saline (or other fluid) supply attached to fluid port 132 can be used in facilitating insertion of the distal tip as is known. Once in the bladder, the operator can view the bladder cavity and associated tissue on the display module 150 using the camera and LED light sources in the tip 112. In 1218 the needle is actuated from "retracted" to the "extended" position by manipulating the actuation tab 510 (shown in FIGS. 5A and 5B) until the sliding mechanism is distally locked. The extended distal tip of the needle 114 is in or near the center of the field of view of the camera module and the operator has a good view of the needle tip on the display module as shown in FIG. 11. In block 1220, the distal end of needle 114 is inserted or jabbed into the bladder tissue by a distal motion or jabbing of the entire endoscope 100. This is in contrast to procedures using a conventional rigid or flexible endoscope wherein the needle assembly is moved relative to the scope for each jab. The pharmaceutical liquid in syringe 180 is dispensed into the tissue. According to some embodiments, the pharmaceutical liquid is or contains botulinum toxin (botox). In block 1222 the process of jabbing and dispensing is repeated to treat as much of the bladder tissue as desired by the operator. In block 1224, the needle is retracted by depressing the lock release button 530 and moving the actuation tab 510 proximally. The needle is thereby retracted back into a recessed position within the tip assembly 110 of tip 112. In block 1226, the cannula and distal tip are withdrawn from the patient's bladder and urethra. In block 1228 single use and multiple use portions of the endoscope 100 are separated from each other. The single use portion can be disposed of and the multiple use portion can be disinfected.

According to some embodiments, the portions of the endoscope that may be come in contact with a patients tissue, such as the distal portion of cannula 120 and the tip assembly 110, are hydrophilic. For further detail relating to hydrophilic treatments, see the co-pending '858 application.

Figure 13:
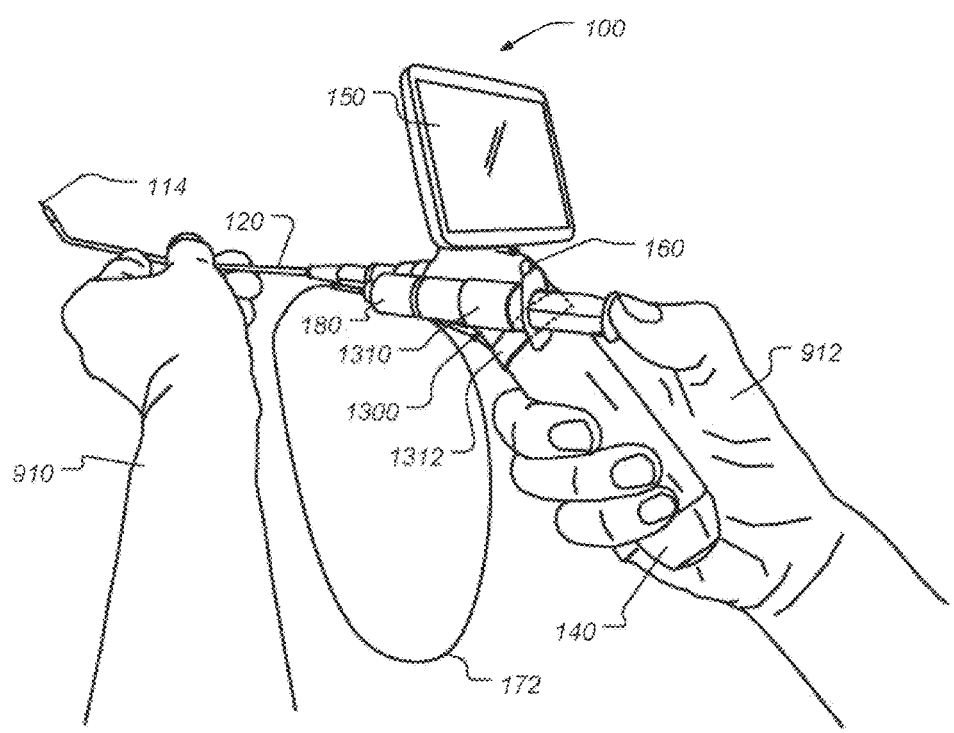
FIGS. 13 and 14 are perspective views of a handheld surgical endoscope having a clip for attaching the syringe to the handle, according to some embodiments.
Figure 14:
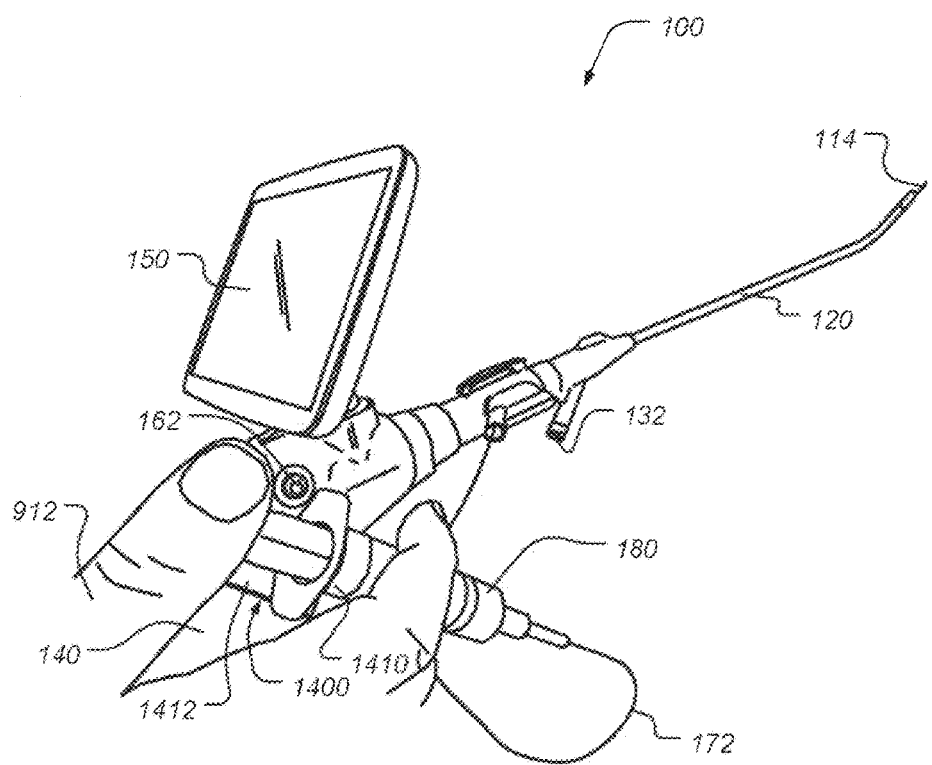

FIGS. 13 and 14 are perspective views of a handheld surgical endoscope having a clip or similar arrangement for attaching the syringe to the handle, according to some embodiments. In these examples, the syringe 180 can be temporarily attached to the handle 140 using a clip or band, which has been found to facilitate performance of the surgical procedure by a single operator in some applications. In the case of FIG. 13, a clip system 1300 is provided that includes a band 1310 to hold syringe 180 and a band 1312 which attaches to the body of handle 140. The two bands 1310 and 1312 can be fixed to each other in the orientation shown such that the syringe 180 is firmly affixed to the handle. With the clip system 1300 installed, the operator can easily use a single hand 912 to grasp the handle 140 and operate its controls (such as image capture button 160) as well as push a plunger of syringe 180. According to some embodiments, the bands 1310 and 1312 are made of a plastic material and according to other embodiments, one or both are made of elastic or rubber-like material. In the case one or both 1310 and 1312 are made of a hard or semi-hard plastic, one or both of the clips can have an opening to facilitate attachment to the handle and/or syringe. Bands 1310 and 1312 can be attached to handle 140 as a unit so that syringe 180 can be slipped in band 1310 and coupled with fluid port 174 via conduit 172 (see FIG. 1). As an alternative, band 1312 can be wrapped around or otherwise attached to handle 140, band 1310 can be wrapped around or otherwise attached to syringe 180, or syringe 180 can be slipped into band 1310, and bands 1310 and 1312 can then be secured to each other, for example by one or more buttons on one that snap-fit into depressions in the other, or by matching hook-and-loop (e.g., Velcro) patches secured, for example by gluing, to each band at appropriate positions. As yet another alternative, a hook-and-loop band can be wrapped around each of syringe 180 and handle 140, and the two bands can then be pressed to each other for a hook-and-loop connection. In this manner, a new syringe can be used for each new patient, or two or more syringes can be used in succession for a single patient, and the syringe can be securely attached to the handle such that the user can operate the syringe and the handle with a single hand (and still has the option to push the syringe plunger with the other hand as needed or desired). Syringe 180 can be attached to the left or the right side of handle 140, and can be tilted at a desired angle relative to the long axis of cannula 120.

FIG. 14 shows another example of a clip system or a similar arrangement for attaching syringe 180 to handle 140. In this case attachment system 1400 includes bands 1410 and 1412 (similar to bands 1310 and 1312) to attach the syringe 180 to handle 140. In the illustrated example, system 1400 is configured to locate the syringe 180 on the right side of handle 140 and also such that the plunger of syringe 180 is tilted slightly upwards as shown. Various other configurations and relative orientations of the positioning of the syringe 180 and the handle 140 are possible and should be implemented depending upon operator ergonomics and preferences for facilitating the particular surgical procedure by a single operator.

Figure 15:
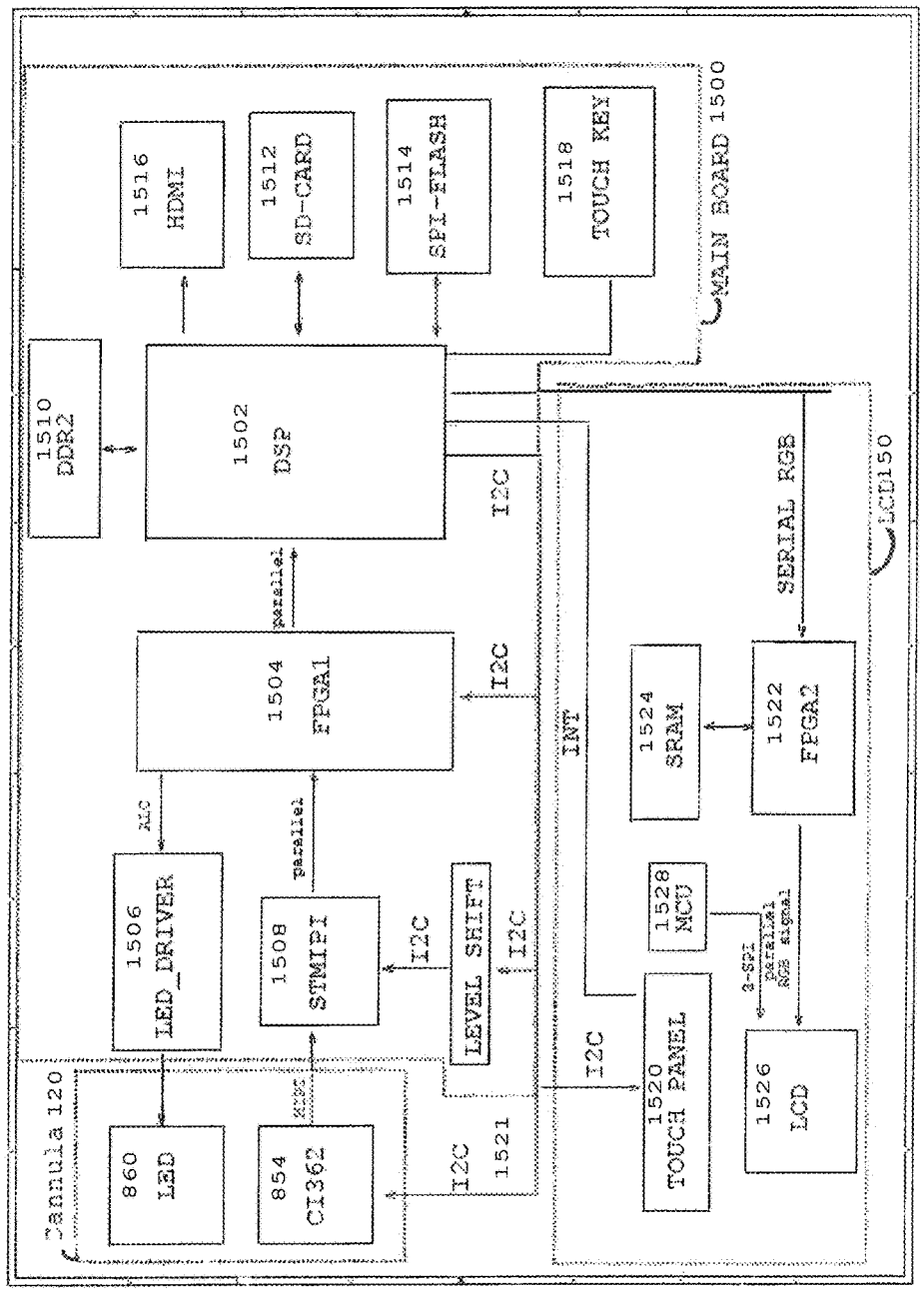
FIG. 15 is a block diagram of the electronics in the single-use and the re-usable portions of one example of the endoscope, according to some embodiments.

FIG. 15 is a block diagram of electronic components in the single-use and in the re-usable portions of one example of the endoscope. The components are in three group: (1) a first group is at the tip of cannula 120; (2) a second group is in a main board 1500 that typically is in handle portion 140; and (3) a third group is in display module 150.

The group of components at the tip of cannula 120 comprises a camera module 854 that preferably is sufficiently small to fit in portion of the lumen such as the upper lumen 430, the largest dimension of which is 2.8 mm in one example of cannula 120. Preferably, the largest dimension of camera module across the length of cannula 120 is less than 2.8 mm, and preferably is even less. Camera module 854 can be, for example, the camera module offered by the OPCOM Group of Taiwan under the designation CI362. Notably, camera module 854 preferably comprises a digital camera, with on-board analog-to-digital conversion, so that its output is a digital signal in a selected format such as a format conforming to the MIPI format specified by MIPI Alliance, Inc. An example of a suitable format is MIPI Camera Serial Interface 2 (MIPI CSI-2), which is a widely adopted, high-speed protocol useful for point-to-point image and video transmission between cameras and host devices. Wires in cannula 120 supply the MIDI format output of camera module 854 to the electrical connectors 310, 312 and thus to main board 1500. One or more LED light sources also are included at the tip of cannula 120.

Main board 1500 serves to interface, process the data and control the components at the tip of cannula 120 and display module 150. In broad terms, main board 1500 supplies power and control signals to camera module 854 and LEDs 860 as well as to display module 150, and converts the camera MIDI format output to an image signal for display on display module 150. In main board 1500, digital signal processor (DSP) is the main processor that controls the operation of the components at the tip of cannula 120 and in display module 150 and process all the captured data. Communicating through field programmable gate array 1 (FPGA1) 1504, DSP 1502 sends a control signal ALC to LED-DRIVER 1506 to turn LEDs 860 ON and OFF and adjust to desired brightness level as needed, and receives the output of camera module 854 after it has been converted from serial to parallel by a STMIPI interface 1508. DSP 1502 exchanges information as needed with information storage devices such as DDR2 memory 1510, SD-CARD memory 1512, and SPI-FLASH memory 1514. DSP 1502 can provide an output to HDMI connector 1516 and can receive key actuation or interrupt signals from touch keys 1518, which can be buttons on handle 140 such as buttons 160 and 162. DSP 1502 also receives touch or swipe information from touch panel 1520 in display panel 150. DSP 1500 provides control signals over I2C line 1522 to cameral module 854, touch panel 1520, and FPGA1 1504. DSP 1502 converts the parallel signal from FPAG1 1504 to a serial RGB signal and supplies the serial RGB signal to display module 150.

Display module 150 displays images from camera module 854 and responds to touch to send control signals to DSP 1502. Display module 150 comprises a field programmable gate array (FPGA2) 1522 that receives images from camera module 854 that are provided from DSP 1502 in serial RGB format. FPGA2 1522 sends the images, in parallel RGB format, to LCD display screen 1526, and can store selected images in memory SRAM 1524 and recall them for display or for storage in SD-CARD 1512 and/or SPI-FLASH 1514, in response to commands from touch panel 1520 or preprogrammed instructions from DSP 1502 or FPGA2 1522 or other processor or memory components. Touch panel 1520 communicates with DSP 1502 over signal bus 12C and also can send commands to DSP 1502 over a direct bus INT. A microcontroller unit MCU 1528 initializes LCD display 1526 as needed and illustrated. Power supply facilities such as a connection to a rechargeable battery removably secured to handle 140, a connection to a manual OFF/ON switch on handle 140, and to a camera control button on handle 140 also can be on main board 1500.

Figure 16:
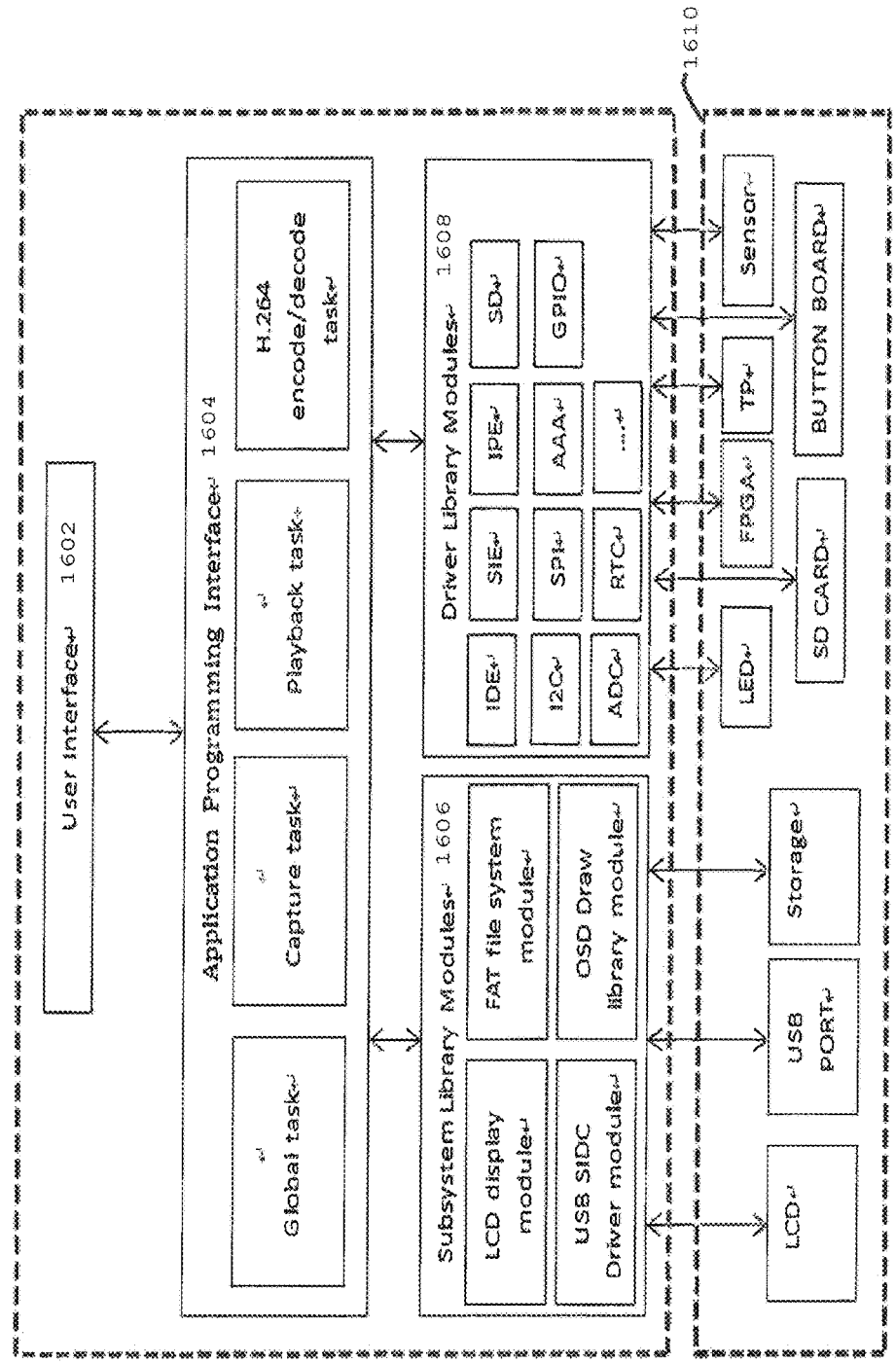
FIG. 16 is a system block diagram of signal flow through a digital signal processor in one example of the endoscope, according to some embodiments.

FIG. 16 illustrates the overall system flow through electronics illustrated in FIG. 15. User interface module 1602 interacts with the user through touch panel 1520, LCD display 1526, and the manual buttons on handle 140, and interacts with an application programming interface 1604. When the endoscope is powered by operating OFF/ON switch 162, DSP 1502 reads firmware in SPI-FLASH 1514 and initiates STMIPI interface 1508, camera module 854, touch panel 1520 and other components of FIG. 15 as needed. Following initiation, application programming interface 1604 directs the indicated tasks (global, capture, playback and encode/decode), responding to commands entered through touch panel 1520 and control button 160 on handle 140, utilizing the indicated subsystem library modules 1606 and driver library modules 1608, which in turn interact with the electronic components 1610 that are the same as the like-named components in FIG. 15.

Figure 17:
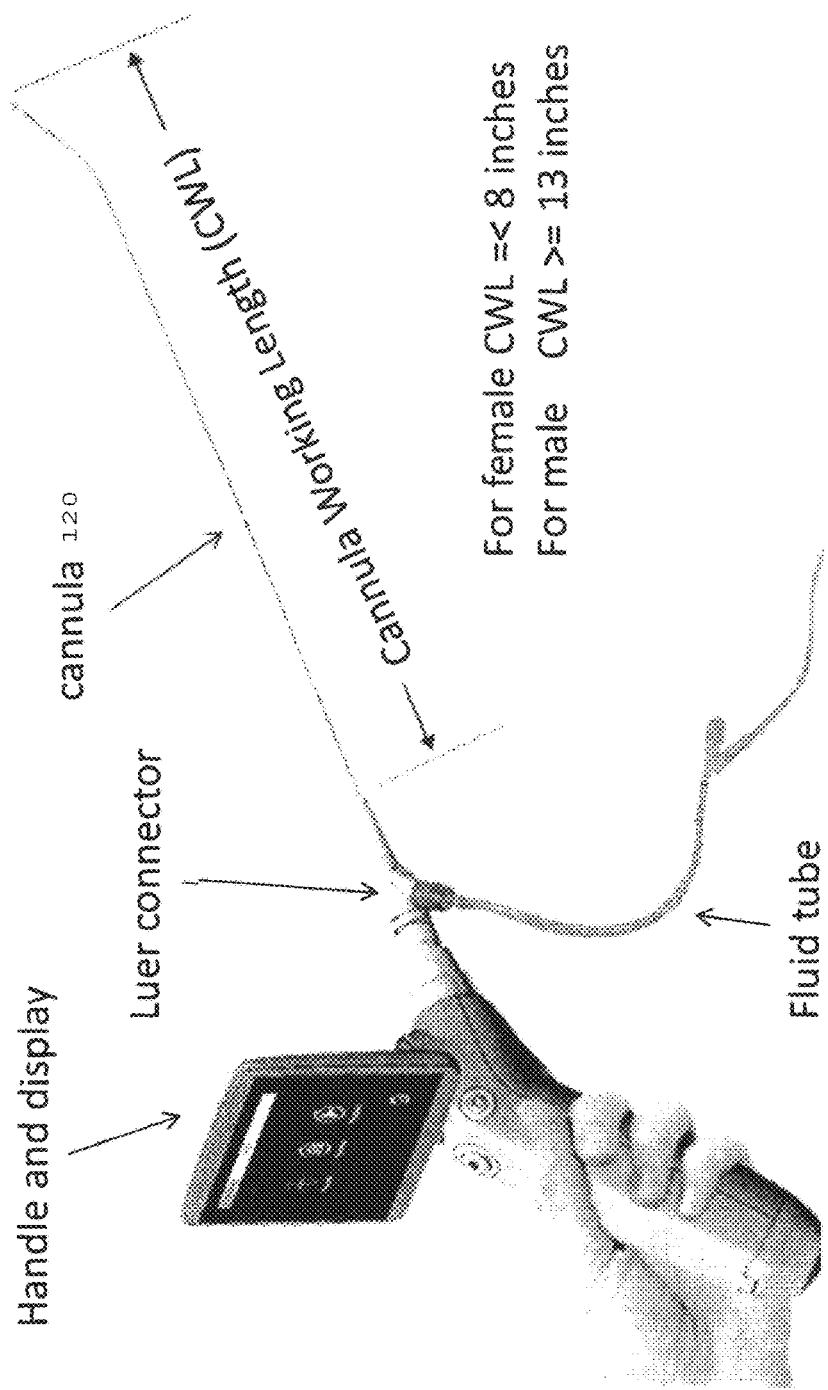
FIG. 17 is a perspective illustration of an example of the endoscope with an indication of the cannula working length that can be different for different cannulas, according to some embodiments.

FIG. 17 illustrates an endoscope that can be otherwise the same as illustrated in the embodiments described above, for example as shown in FIG. 9, but is provided with plural cannulas 120 that differ in cannula working length (CWL). In one example, cannulas with two CWL can be provided: a shorter cannula with CWL of 8 inches or less, suitable for bladder inspection mainly of female patients, and a longer cannula with CWL of 13 inches or more, suitable for bladder inspection mainly of male patents. Of course, these lengths are only examples, and different lengths can be provided for different medical applications, and three or more different CWL can be provided. An important benefit of providing cannulas with plural CWLs is that each CWL can be optimized for a respective medical application, and a medical facility such as an office, clinic, or hospital can stock as many different CWL cannulas as appropriate for its practice and can use for a given patient procedure the cannula that is best suited for that procedure. For example, in cystoscopy an optimal CWL may be about 8 inches for most female patients but a much greater CWL may present problems such as undesirable bending and twisting of the cannula during insertion and during visualization of the bladder. As another example, for male patient cystoscopy a CWL that is too low may not be sufficient to reach the bladder. For medical applications other than cystoscopy, other CWLs may be appropriate, such as in the range of 8-13 inches, more specifically the range of 10-12 inches, the range of 11-12 inches, or about 11 inches. As illustrated, CWL is measured from where cannula 120 emerges from fluid hub and connection assembly 130 to the distal tip of cannula 120. In the case of greater CWLs, a guide wire can be inserted or added to cannula 120, for example in fluid channel(s) or lumen(s) in cannula 120, or through a dedicated additional channel or lumen, or can be integrated or attached to a wall of cannula 120.

Figure 18:
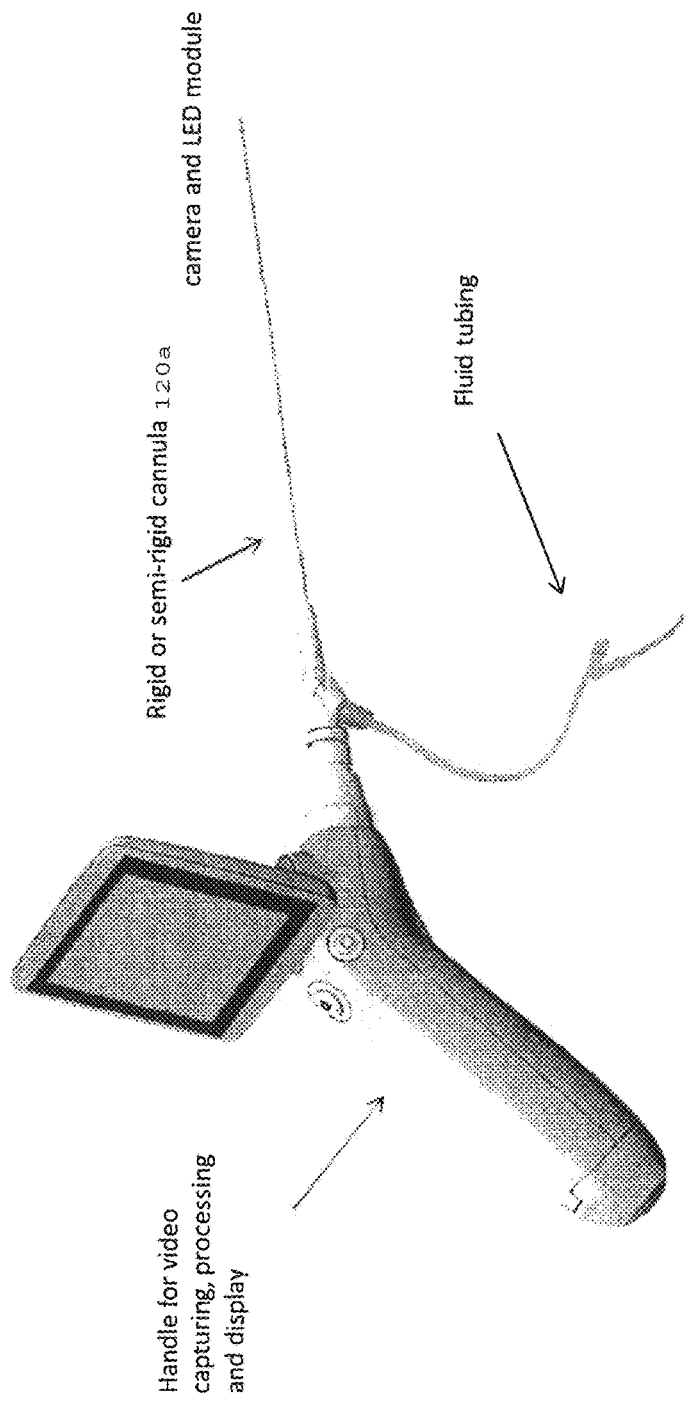
FIG. 18 illustrates an endoscope that has a rigid or semi-rigid cannula, according to some embodiments.

FIG. 18 illustrates an endoscope that can be otherwise the same as illustrated in the embodiments described above, such as shown in FIG. 9, but has a rigid or semi-rigid cannula 120*a*. The term rigid in this context denotes a rigidity that keeps cannula 120*a* from bending noticeably when being inserted and used in a patient's body, and the term semi-rigid denotes lesser rigidity that allows some bending and avoid injuries or perforation but not enough to interfere with the medical procedure in which the endoscope is used. Cannula 120*a* can be straight, as seen in FIG. 18, or it can be provided with a curved tip or with curvature along some or all of its length, as desirable for respective medical procedures.

Figure 19:
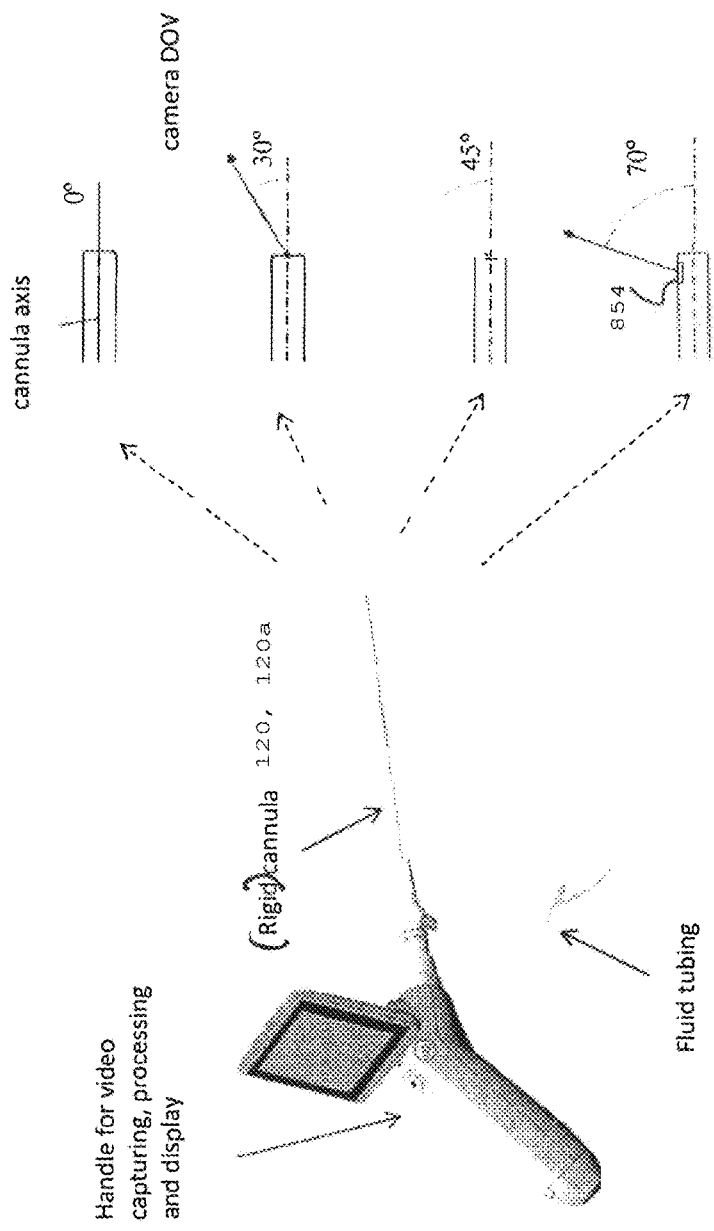
FIG. 19 illustrates an endoscope that also has a rigid or semi-rigid cannula but can be configured with different directions of view (DOV) of the camera at the cannula tip, according to some embodiments.

FIG. 19 illustrates an endoscope that can be otherwise the same as in the embodiments described above but can be configured with a selected direction of view (DOV) of camera module 854. For example, FIG. 19 illustrates at upper right a DOV of zero degrees, i.e., the direction of view is along the long axis of the cannula tip, or of the entire cannula if the cannula tip is not angled relative to the rest of the cannula 120. While FIG. 19 labels the cannula "rigid," the illustrated DOVs can be for cannulas that are semi-rigid or more flexible. FIG. 19 further illustrates at right that different DOVs can be selected for different cannulas 120, 120a, such as an angle of 30 degrees, 45 degrees, or 70 degrees. In the case of DOVs at greater angles to the cannula tip length, the camera can be at a side of the cannula tip, such as illustrated for camera module 854 at bottom right in FIG. 19. The illustrated angles are only examples, and different angles can be selected for respective cannulas depending on the medical procedure to be performed or the preference of the health professional carrying out the medical procedure.

Figure 20:
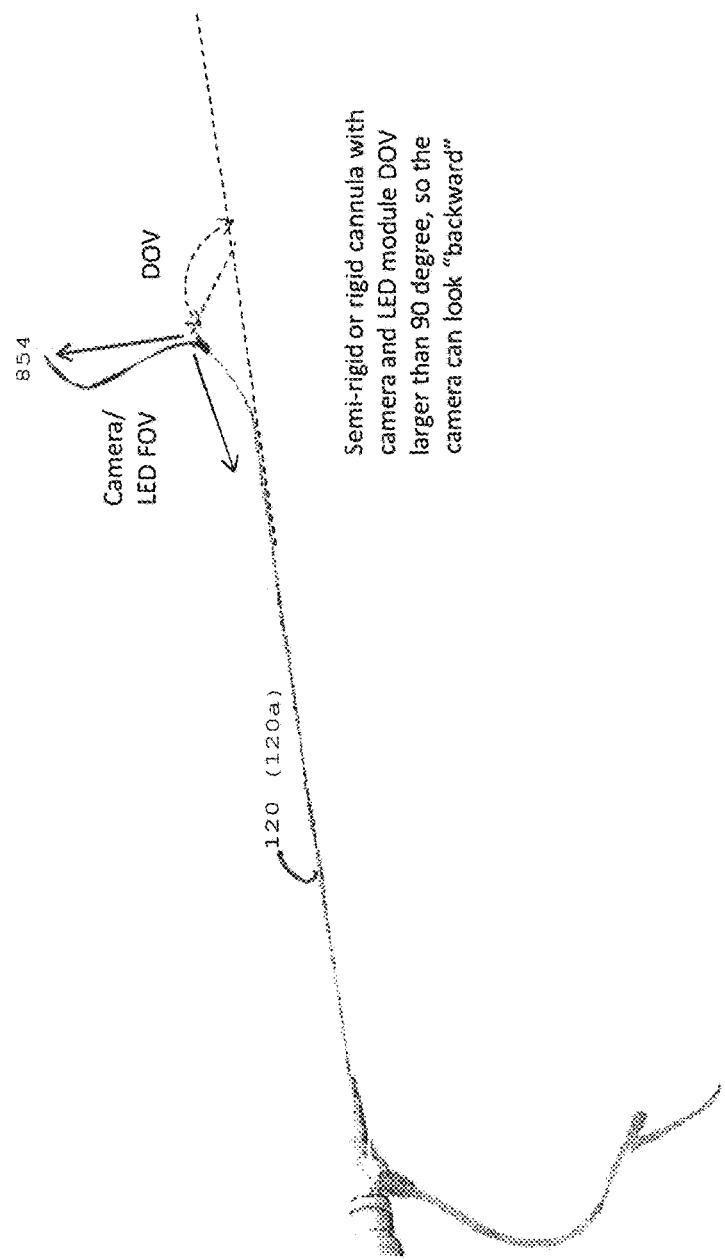
FIG. 20 illustrates an endoscope that can be configured with directions of view (DOV) of the camera at the cannula tip that exceed a right angle to the cannula length and can even operate with the camera looking backward, according to some embodiments.

FIG. 20 illustrates an endoscope that can be otherwise the same as in the embodiments described above but can be configured with direction of view (DOV) of camera module 854 that allows imaging of tissue that is behind (proximal) of the cannula tip. In this case, camera module can be mounted at the side of the cannula tip and can even be tilted relative to the long axis of the cannula so as to point at least partly in the proximal direction of the endoscope and cannula. Again, while FIG. 20 illustrates the case of a rigid or semi-rigid cannula (but with an angled tip), the cannula can be more flexible and can include a guide wire if desired.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What it claimed is:

1. An endoscope with a single-use, disposable distal portion with a digital camera module at the tip and a reusable proximal portion, configured to enable a single user to operate the endoscope in a medical procedure that includes visualizing an internal region of a patient, comprising:
    a handle configured to be grasped by the user's hand and having at least one button controlling endoscope functions, and a video display screen mechanically attached to the handle, wherein both the handle and the screen form a part of the reusable portion of the endoscope;
    a cannula having a tip and forming a part of the disposable portion of the endoscope and configured with one or more internal lumens;
    a connector at a proximal part of the disposable portion of the endoscope, configured to releasably mate tool-free with a connector at the reusable portion of the endoscope thereby releasably integrating the reusable and disposable portions for use in a medical procedure and detach tool-free from the reusable portion for disposal of the disposable portion after the medical procedure;
    a light source and an imaging module with a video camera at a distal portion of the cannula, coupled with the screen to illuminate the region in the patient and provide images of the region to the screen under the control of said buttons on the handle;
    wherein the video camera is a digital camera providing a digital signal representing one or more images, and transmits the digital signal from the cannula tip to the handle;
    wherein the digital video camera has dimensions in a direction across a long dimension of the cannula tip that is less than 5 mm; and
    an injection needle permanently mounted at the cannula tip and movable between a retracted position in which the needle is entirely within the cannula and an extended position in which the needle protrudes distally from the cannula; and
    wherein said cannula, with said injection needle permanently mounted therein, is in a sterile package from which it is removed before use;
    thereby enabling a single user holding the handle to use one hand to insert and retract the cannula in and from the patient, operate said at least one button, use the same or the other hand to selectively force fluid into said injection needle, and selectively move the injection needle to its extended position and force the needle into a selected region of patient tissue by moving the entire endoscope.

2. The endoscope of claim 1, in which the digital signal from the video camera conforms to a standard for transmission of video data from a camera module to a host specified by MIDI Alliance, Inc.

3. The endoscope of claim 1, in which the digital signal transmitted from the video camera is in serial format, and further including an interface formatting said serial format signal to parallel format.

4. The endoscope of claim 1, further including a digital signal processor formatting said digital signal transmitted from the video camera into an RGB (red/green/blue) signal for display on said screen.

5. The endoscope of claim 1, in which the cannula comprises two or more cannulas having different cannula working lengths (CWLs), of which only one cannula is integrated with the reusable portion at any one time.

6. The endoscope of claim 5, in which one of the cannulas has a CWL in the range of 8 inches or less and another has a CWL in the range of 13 inches or more.

7. The endoscope of claim 1, in which the cannula is rigid.

8. The endoscope of claim 1, in which the cannula is semi-rigid or with variable rigidity depending on the distance from the distal tip.

9. The endoscope of claim 1 in which the cannula tip is angled relative to the remainder of the cannula.

10. The endoscope of claim 1, in which the entirety of the cannula is straight.

11. The endoscope of claim 1, in which the video camera has a direction of view (DOV) that is angled relative to a direction in which the cannula tip extends.

12. The endoscope of claim 11, in which the DOV is angled at 30 degrees or more.

13. The endoscope of claim 11, in which the DOV is angled at 90 degrees or more.

14. The endoscope of claim 1, further including a guide wire extending along the cannula to guide the cannula during insertion into a patient and/or visualization of a patient's organ.

15. An endoscope with a single-use, disposable distal portion with a digital camera module at the tip and a reusable proximal portion, configured to enable a single user to operate the endoscope in a medical procedure that includes visualizing an internal region of a patient, comprising:

- a handle configured to be grasped by the user's hand and having at least one button controlling endoscope functions, and a video display screen mechanically attached to the handle, wherein both the handle and the screen form a part of the reusable portion of the endoscope;
- a cannula having a tip and forming a part of the disposable portion of the endoscope and configured with one or more internal lumens;
- a connector at a proximal part of the disposable portion of the endoscope, configured to releasably mate tool-free with a connector at the reusable portion of the endoscope thereby releasably integrating the reusable and disposable portions for use in a medical procedure and detach tool-free from the reusable portion for disposal of the disposable portion after the medical procedure;
- a light source and an imaging module with a video camera at a distal portion of the cannula, coupled with the screen to illuminate the region in the patient and provide images of the region to the screen under the control of said buttons on the handle;
- wherein the video camera is a digital camera providing a digital signal representing one or more images, and transmits the digital signal from the cannula tip to the handle;
- wherein the digital video camera has dimensions in a direction across a long dimension of the cannula tip that is less than 5 mm;
- an injection needle permanently mounted at the cannula tip and movable between a retracted position in which the needle is entirely within the cannula and an extended position in which the needle protrudes distally from the cannula; and
- a needle actuator at a proximal portion of the disposable portion, coupled with said injection needle and movable by hand between a position in which the actuator forces the needle to its retracted position and a position in which the actuator forces the needle to its extended position;
- thereby enabling a single user holding the handle to use one hand to insert and retract the cannula in and from the patient, operate said at least one button, use the same or the other hand to selectively force fluid into said injection needle, and selectively move the injection needle to its extended position and force the needle into a selected region of patient tissue by moving the entire endoscope.

* * * * *